(12) United States Patent
Dey et al.

(10) Patent No.: US 7,892,737 B2
(45) Date of Patent: Feb. 22, 2011

(54) COMPOSITIONS, KITS AND METHODS PERTAINING TO STABILITY MODULATION OF PNA OLIGOMER/NUCLEIC ACID COMPLEXES

(75) Inventors: Subhakar Dey, North Billerica, MA (US); Eric G. Anderson, Redwood City, CA (US)

(73) Assignee: Life Technologies Corporation, Carlsbad, CA (US)

( * ) Notice: Subject to any disclaimer, the term of this patent is extended or adjusted under 35 U.S.C. 154(b) by 940 days.

(21) Appl. No.: 11/477,240

(22) Filed: Jun. 29, 2006

(65) Prior Publication Data

US 2007/0003966 A1 Jan. 4, 2007

Related U.S. Application Data

(60) Provisional application No. 60/695,796, filed on Jun. 30, 2005.

(51) Int. Cl.
*C12Q 1/68* (2006.01)
*C07H 21/00* (2006.01)
*C07H 21/02* (2006.01)

(52) U.S. Cl. .......................... 435/6; 536/23.1; 536/24.3; 536/25.3; 536/26.6

(58) Field of Classification Search ...................... 435/6; 536/23.1, 24.3, 25.3, 26.6
See application file for complete search history.

(56) References Cited

U.S. PATENT DOCUMENTS

| | | | |
|---|---|---|---|
| 6,355,421 B1 | 3/2002 | Coull et al. | |
| 6,355,726 B1 | 3/2002 | Doemling et al. | |
| 6,358,679 B1 | 3/2002 | Heid et al. | |
| 6,911,426 B2 | 6/2005 | Reed et al. | |
| 2002/0177133 A1 | 11/2002 | Egholm et al. | |
| 2003/0077608 A1 | 4/2003 | Coull et al. | |
| 2004/0034191 A1 | 2/2004 | Manoharan et al. | |

FOREIGN PATENT DOCUMENTS

WO  WO98/03542  1/1998

OTHER PUBLICATIONS

Bleczinski, C.F. et al, "Steroid-DNA Interactions Increasing Stability, Sequence-Selectivity, DNA/RNA Discrimination, and Hypochromicity of Oligonucleotide Duplexes", J. Am. Chem. Soc. 1999, 121, pp. 10889-10894.
Challa, H. et al, "Nitroazole Universal Bases in Peptide Nucleic Acids", Organic Letters, 1999 vol. 1, No. 10, pp. 1639-1641, American Chemical Society.
Garner, P. et al, "Enhancement of αPNA Binding Affinity and Specificity through Hydrophobic Interactions", ChemBioChem 2001, No. 3, pp. 224-226.
Gryaznov, S.M. et al, "Modulation of oligonucletide duplex and triplex stability via hydrophobic interactions", Nucleic Acids Research, 1993, vol. 21, No. 25, pp. 5909-5915.
Guckian, K.M. et al, "Factors Contributing to Aromatic Stacking in Water: Evaluation in the Context of DNA", J. Am. Chem. Soc. 2000, 122, pp. 2213-2222.
Kohler O. et al, "Forced Intercalation Probes (FIT Probes) : Thiazole Orange as a Fluorescent Base in Peptide Nucleic Acids for Homogeneous Single-Nucleotide-Polymorphism Detection", ChemBioChem Full Papers, 2005, 6, pp. 69-77.
Lagriffoule, P. et al, "Peptide Nucleic Acids with a Conformationally Constrained Chiral Cyclohexyl-Derived Backbone", Chem. Eur. J. 1997, 3, No. 6, pp. 912-919.
Letsinger, R.L. et al, "Cholesteryl-conjugated oligonucleotides: Synthesis, properties, and activity as inhibitors of replication of human immunodeficiency virus in cell culture", Proc. Natl. Acad. Sci. USA, vol. 86, pp. 6553-6556, Sep. 1989.
Petersheim, M. et al, "Base-Stacking an dBase-Pairing Contributions to Helix Stability: thermodynamics of Double-Helix Formation with CCGG, CCGGp, CCGGAp, ACCGGp, CCGGUp, and ACCGGUp", Biochemistry 1983, 22, pp. 256-263.
Seela, F. et al, "The $N^8$-(2'-deoxyribofuranoside) of 8-aza-7-deazaadenine: a universal nucleoside forming specific hydrogen bonds with the four canonical DNA constituents", Nucleic Acids Research, 2000, vol. 28, No. 17, pp. 3224-3232.
Senior, M. et al, "Influence of Dangling Thymidine Residues on the Stability and structure of Two DNA Duplexes", Biochemistry 1988, 27, pp. 3879-3885.
Zhang, P. et al, "Peptide Nucleic Acid-DNA Duplexes Containing the Universal Base 3-Nitropyrrole", Methods, 23, pp. 132-140.
PCT International Search Report mailed Mar. 30, 2007.

*Primary Examiner*—Jezia Riley

(57) ABSTRACT

This invention is related to methods, kits and compositions pertaining to stability modulation of PNA oligomer/nucleic acid complexes.

35 Claims, 16 Drawing Sheets

General structure of an exemplary PNA oligomer

B' = -OH or -NH$_2$
z = 0 - 100
Nb = a nucleobase or ligand

Condensation of the N-terminal amine of an exemplary PNA oligomer with a label comprising a carboxylic acid group B' = -OH or -NH$_2$
z = 0 - 100
Nb = a nucleobase or ligand Mono or Bis alkylation of the N-terminal amine of an exemplary PNA oligomer Exemplary method for indirect labeling of the C-terminus of a PNA oligomer Pg = protecting group
Nb = a nucleobase or ligand Condensation of the C-terminal carbonyl carbon of an exemplary PNA oligomer with a label comprising an amine group Pg = protecting group
z = 0 - 100
Nb = a nucleobase or ligand Condensation of an exemplary PNA oligomer comprising a C-terminal hydrophobic group to a solid support Nb = a nucleobase or ligand General structure of an exemplary bis labeled PNA oligomer B' = -OH or -NH$_2$
z = 0 - 100
Nb = a nucleobase or ligand Structures of two possible PNA oligomers comprising an N-terminal hydrophobic group and a detectable moiety B' = -OH or -NH$_2$
z = 0 - 100
Nb = a nucleobase or ligand
Flu = 5(6) carboxyfluorescein Structure of a PNA oligomer comprising two hydrophobic groups, an energy donor moiety and an energy acceptor moiety B' = -OH or -NH$_2$
z = 0 - 100
Nb = a nucleobase or ligand
Flu = 5(6) carboxyfluorescein; Dab = dabcyl Structure of a PNA oligomer comprising two hydrophobic groups, an energy donor moiety and an energy acceptor moiety B' = -OH or -NH$_2$
z = 0 - 100
Nb = a nucleobase or ligand
Flu = 5(6) carboxyfluorescein; Dab = dabcyl Structure of a PNA oligomer comprising two hydrophobic groups, an energy donor moiety and an energy acceptor moiety z = 0 - 100
Nb = a nucleobase or ligand
Flu = 5(6) carboxyfluorescein; Dab = dabcyl Structure of a PNA oligomer comprising two hydrophobic groups, two charged amino acids, an energy donor moiety and an energy acceptor moiety z = 0 - 100
Nb = a nucleobase or ligand
Flu = 5(6) carboxyfluorescein; Dab = dabcyl

CH₃CONH-GTA-TAC-AAG-T-CONH₂

III - Acetylated PNA oligomer

CONH-GTA-TAC-AAG-T-CONH₂

IV - Cyclohexyl butyrylated PNA oligomer

COMPOSITIONS, KITS AND METHODS PERTAINING TO STABILITY MODULATION OF PNA OLIGOMER/NUCLEIC ACID COMPLEXES

CROSS REFERENCE TO RELATED APPLICATIONS

This application claims priority to U.S. Provisional Application No. 60/695,796 filed Jun. 30, 2005.

The section headings used herein are for organizational purposes only and are not to be construed as limiting the subject matter described in any way.

1. FIELD

This invention is related to the field of peptide nucleic acids.

2. INTRODUCTION

Peptide nucleic acid (PNA) is a class of synthetic nucleobase comprising oligomers that can sequence specifically hybridize to nucleic acids and other polynucleobase strands. Hybridization between nucleobases of polynucleobase strands typically follows well-established rules for hydrogen bonding. For Watson-Crick base pairing, typically adenine (A) base pairs with thymine (T) and cytosine (C) base pairs with guanine (G). Various other base-pairing motifs are well known in the nucleic acid arts.

A nucleoside comprising the nucleobase 8-aza-7-deazaadenine (8-A-7-DAA) has been investigated and found to exhibit properties of a universal nucleoside (Seela et al. *Nucl. Acids Res.*, 28(17): 3224-3232 (2000). The term universal nucleoside refers to a nucleoside that forms specific hydrogen bonds towards the four canonical DNA nucleobases (i.e. adenine, thymine, cytosine and guanine). Several universal nucleobases have been proposed as being suitable for use in PNA oligomers (Challa et al., *Organic Letters*, 1(10): 1639-1641 (1999) & Zhang et al., *Methods*, 23: 132-140 (2001)). Theoretically, a universal nucleobase should form specific hydrogen bonds towards any of the four canonical DNA nucleobases.

Libraries of short PNA oligomers that can be ligated to produce longer PNA oligomers are of interest as a means to facilitate the rapid preparation of probes needed for large scale genome analysis projects (See for example: US Patent Application Publication No. 2003-0077608). However, it would be useful to have available all of the probes needed for such large scale genome analysis projects without having to expend the labor needed to ligate the many short PNA oligomers into many longer oligomers. Moreover, even if ligation is used to prepare the PNA oligomer, it might be beneficial if shorter probes could be used in the hybridization assays.

Regardless, the preparation of a library of full sized PNA oligomer is difficult since the minimum probe length is roughly a 10-mer given that shorter probes (for unmodified PNAs) will typically have a thermal melting temperature ($T_m$) so low that hybridization does not occur under conditions typically used for robust hybridization analysis. Assuming 10-mer probes of the library comprise the four naturally occurring nucleobases (A, C G & T), the total number of probes needed to make a complete library set would be 1,048,576 ($4^{10}$) different probes. Given the large number of probes required to complete the set, the production of such a library is simply not economically feasible at this time.

However the application of certain techniques could possibly reduce the number of different probes needed to form a complete set and thereby facilitate the production of a useful library. For example, a universal base could be used for some of the positions. This would reduce the complexity of the library because instead of having four different possible bases at each position, only one base would be needed. For example, if a universal base was used at four of the ten positions in a 10-mer, a total of 4096 ($4^6$) different probes would complete the set.

Furthermore, even fewer probes might be needed to complete a set if it was possible to raise the $T_m$ of the probes of the set in a sequence independent manner. For example, if it were possible to raise the average melting temperature of all probes of a set by approximately 10-15° C. in a substantially sequence independent manner, it might be possible to use 8-mer or 9-mer probe sets. The production of probe sets wherein the $T_m$ can be modulated (e.g. elevated) in a substantially sequence independent manner is one possible application for the embodiments of the invention about to be described.

3. DRAWINGS

The skilled artisan will understand that the drawings, described below, are for illustration purposes only. The drawings are not intended to limit the scope of the present teachings in any way.

All literature and similar materials cited in this application, including but not limited to, patents, patent applications, articles, books, treatises, and internet web pages, regardless of the format of such literature and similar materials, are expressly incorporated by reference herein in their entirety for any and all purposes.

4. DEFINITIONS

Figure 1A:
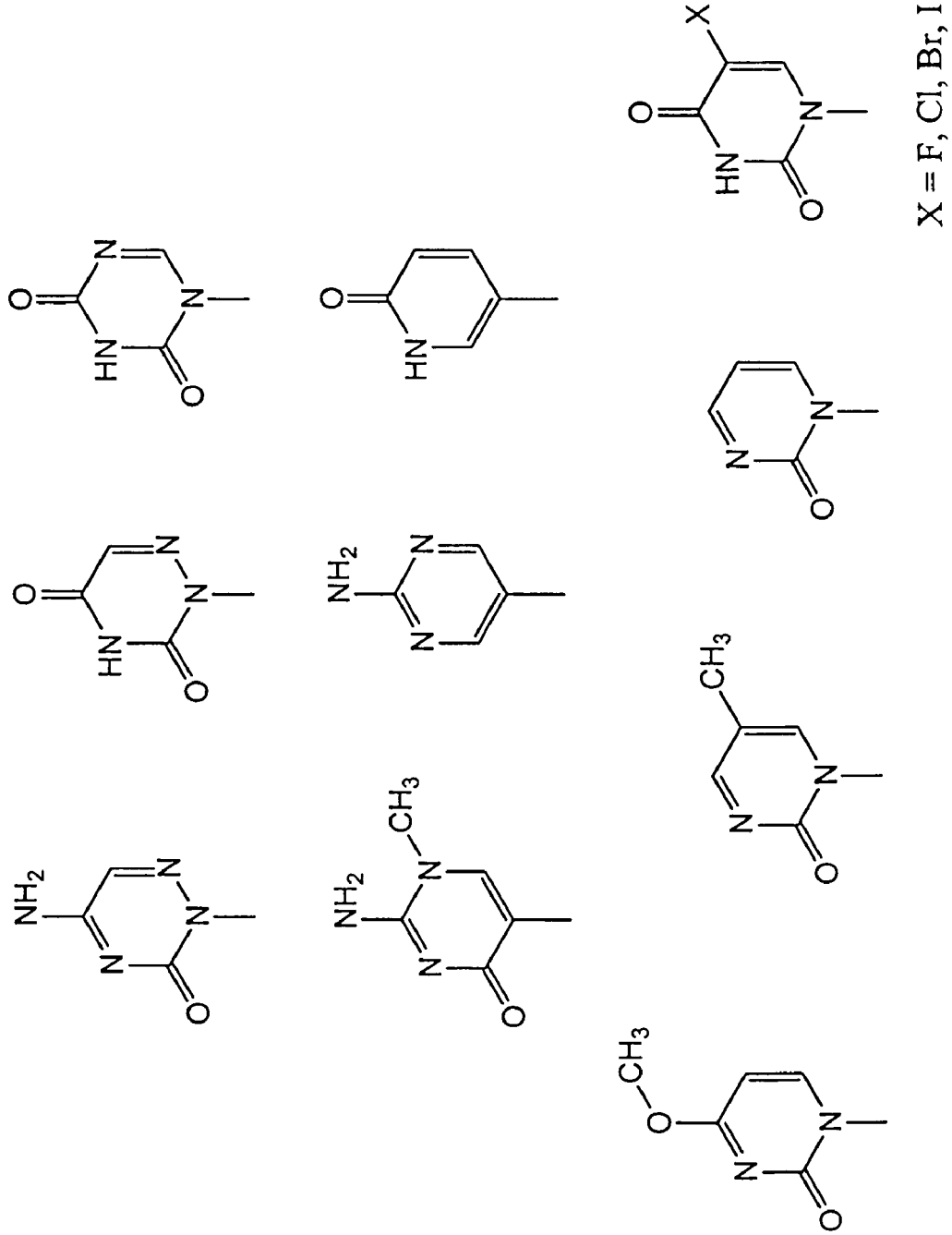
FIGS. 1A and 1B are illustrations of some nucleobases that can be incorporated into nucleic acids, PNA oligomers and PNA chimeras.
Figure 1B:
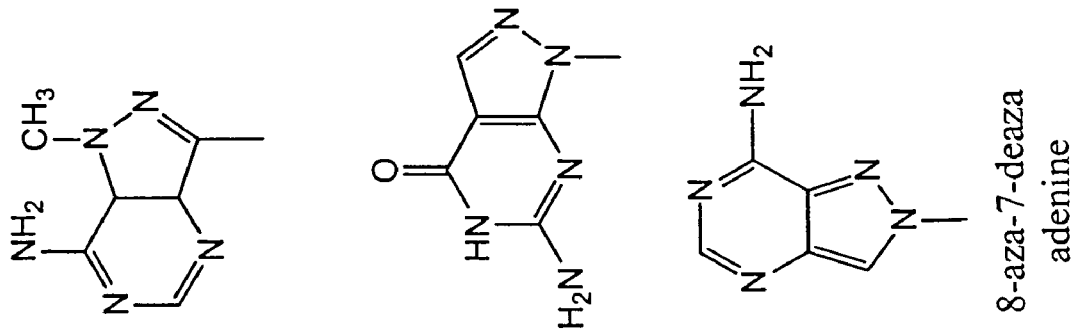
Figure 1B:
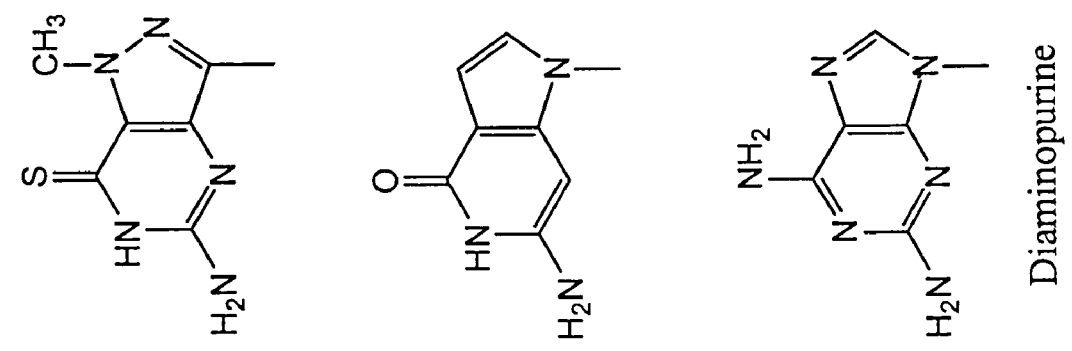
Figure 1B:
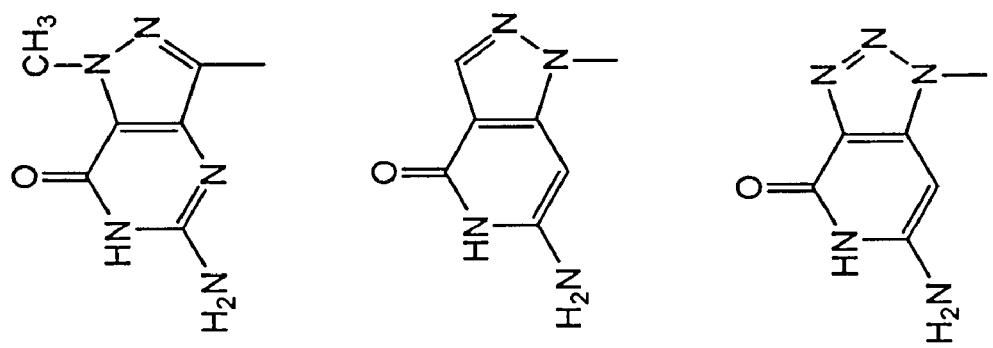
Figure 1B:
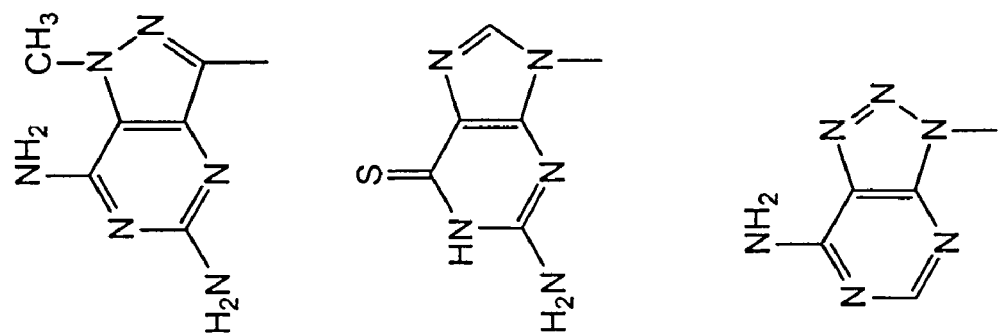

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall control.

a. As used herein, "nucleobase" refers to those naturally occurring and those non-naturally occurring heterocyclic moieties commonly known to those who utilize nucleic acid technology or utilize peptide nucleic acid technology to thereby generate polynucleobase strands that can sequence specifically bind to nucleic acids and other polynucleobase strands. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine). Other non-limiting examples of suitable nucleobase include those nucleobases illustrated in FIGS. 1A and 1B (also see FIGS. 2A and 2B of U.S. Pat. No. 6,357,163).

b. As used herein, "nucleobase sequence" refers to any segment, or aggregate of two or more segments (i.e. linked polymer), of a polynucleobase strand. Non-limiting examples of suitable polynucleobase strands include oligodeoxynucleotides (e.g. DNA), oligoribonucleotides (e.g. RNA), peptide nucleic acids (PNA), PNA chimeras, nucleic acid analogs and/or nucleic acid mimics.

c. As used herein, "target sequence" refers to a nucleobase sequence of a polynucleobase strand sought to be determined.

d. As used herein, the phrase "nucleobase containing subunit" refers to a subunit of a polynucleobase strand that comprises a nucleobase. For oligonucleotides, the nucleobase containing subunit is a nucleotide. With reference to oligonucleotides, those of skill in the art will appreciate the form of a subunit associated with other species of polynucleobase strands.

e. As used herein, "polynucleobase strand" refers to a complete single polymer strand comprising two or more nucleobase-containing subunits.

f. As used herein, "nucleic acid" refers to a polynucleobase strand having a backbone formed solely from nucleotides, or analogs thereof. Preferred nucleic acids are DNA, RNA, L-DNA or locked nucleic acids (LNA). For the avoidance of any doubt, PNA is a nucleic acid mimic and not a nucleic acid or nucleic acid analog. PNA is not a nucleic acid since it is not formed from nucleotides. For purposes of interpreting this specification, a PNA chimera (peptide nucleic acid/nucleic acid chimera) is not a nucleic acid.

g. As used herein, "peptide nucleic acid" or "PNA" refers to any polynucleobase strand or segment of a polynucleobase strand comprising two or more PNA subunits, including, but not limited to, any polynucleobase strand or segment of a polynucleobase strand referred to or claimed as a peptide nucleic acid in U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053, 6,107,470 and 6,357,163. For the avoidance of any doubt, as used herein a PNA oligomer includes PNA chimeras.

The term "peptide nucleic acid" or "PNA" shall also apply to any polynucleobase strand or segment of a polynucleobase strand comprising two or more subunits of those nucleic acid mimics described in the following publications: Lagriffoul et al., *Bioorganic & Medicinal Chemistry Letters*, 4: 1081-1082 (1994); Petersen et al., *Bioorganic & Medicinal Chemistry Letters*, 6: 793-796 (1996); Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Diederichsen, U., *Bioorganic & Medicinal Chemistry Letters*, 7: 1743-1746 (1997); Lowe et al., *J. Chem. Soc. Perkin Trans.* 1, (1997) 1: 539-546; Lowe et al., *J. Chem. Soc. Perkin Trans.* 11: 547-554 (1997); Lowe et al., *J. Chem. Soc. Perkin Trans.* 1 1:5 55-560 (1997); Howarth et al., *J. Org. Chem.* 62: 5441-5450 (1997); Altmann, K-H et al., *Bioorganic & Medicinal Chemistry Letters*, 7: 1119-1122 (1997); Diederichsen, U., *Bioorganic & Med. Chem. Lett.*, 8: 165-168 (1998); Diederichsen et al., *Angew. Chem. Int. Ed.*, 37: 302-305 (1998); Cantin et al., *Tett. Lett.*, 38: 4211-4214 (1997); Ciapetti et al., *Tetrahedron*, 53: 1167-1176 (1997); Lagriffoule et al., *Chem. Eur. J.*, 3: 912-919 (1997); Kumar et al., *Organic Letters* 3(9): 1269-1272 (2001); and the Peptide-Based Nucleic Acid Mimics (PENAMs) of Shah et al. as disclosed in WO96/04000.

In some embodiments, a "peptide nucleic acid" or "PNA" is a polynucleobase strand or segment of a polynucleobase strand comprising two or more covalently linked subunits of the formula:

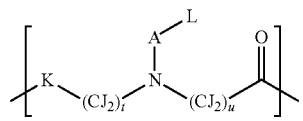

wherein, each J is the same or different and is selected from the group consisting of: H, R', OR', SR', NHR', NR'$_2$, F, Cl, Br and I. Each K is the same or different and is selected from the group consisting of: O, S, NH and NR'. Each R' is the same or different and can be an alkyl group, alkenyl group, alkynyl group, heteroalkyl group, heteroalkenyl group, heteroalkynyl group or heterocyclohydrocarbon group. For example, R' can be methyl, ethyl, n-propyl, isopropyl, n-butyl, sec-butyl, tert-butyl, iso-butyl, n-pentyl, n-hexyl, methoxy, ethoxy, benzyl or phenyl.

Each A is a single bond, a group of the formula; —(CJ$_2$)$_s$— or a group of the formula; —(CJ$_2$)$_s$C(O)—, wherein, J is defined above and each s is a integer from one to five. Each t is 1 or 2 and each u is 1 or 2. Each L is the same or different and is independently adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine), N8-(8-aza-7-deazaadenine), other naturally occurring nucleobase analogs or other non-naturally occurring nucleobases (e.g. FIGS. 1A and 1B).

In some embodiments, a PNA subunit can be a naturally occurring or non-naturally occurring nucleobase attached to the N-α-glycyl nitrogen of the N-[2-(aminoethyl)]glycine backbone through a methylene carbonyl linkage; this currently being the most commonly used form of a peptide nucleic acid subunit.

h. As used herein, "PNA chimera" means an oligomer or polymer segment comprising two or more PNA subunits and one or more nucleic acid subunits (i.e. DNA or RNA), or analogs thereof. PNA subunits and the nucleic acid subunits can be linked to the other by a covalent bond or by a linker. For example, a PNA/DNA chimera could comprise at least two PNA subunits covalently linked, via a chemical bond, to at least one 2'-deoxyribonucleic acid subunit (For exemplary methods and compositions related to PNA chimera preparation see: U.S. Pat. No. 6,063,569). For purposes of this invention, a PNA chimera includes a combination of different types of nucleobases containing subunits (e.g. PNA, DNA, RNA) but the mere incorporation of amino acid subunits, such as glycine, or one or more labels or linkers, does not mean that an oligomer is PNA chimera. Furthermore, for the avoidance of any doubt a nucleoside or nucleotide is not an alkyl, alkylene, alkenyl, alkynyl, heteroalkyl, heteroalkenyl, heteroalkynyl or heterocyclohydrocarbon group for purposes of interpreting this specification.

i. As used herein, "sequence specifically" refers to hybridization by base pairing through hydrogen bonding. Non-limiting examples of standard base pairing include adenine base pairing with thymine or uracil and guanine base pairing with cytosine. Other non-limiting examples of base-pairing motifs include, but are not limited to: adenine base pairing with any of: 5-propynyl-uracil, 2-thio-5-propynyl-uracil, 2-thiouracil or 2-thiothymine; guanine base pairing with any of: 5-methylcytosine or pseudoisocytosine; cytosine base pairing with any of: hypoxanthine, N9-(7-deaza-guanine) or N9-(7-deaza-8-aza-guanine); thymine or uracil base pairing with any of: 2-aminopurine, N9-(2-amino-6-chloropurine) or N9-(2,6-diaminopurine); and N8-(8-A-7-DAA), being a universal base, base pairing with any other nucleobase, such as for example any of: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine or N9-(7-deaza-guanine).

j. As used herein, the term "linked polymer" refers to a polynucleobase strand comprising two or more polymer segments that are linked by a linker. The polymer segments that can be linked to form the linked polymer can be an oligodeoxynucleotide, an oligoribonucleotide, a peptide, a polyamide, a peptide nucleic acid (PNA) or a PNA chimera. In some embodiments, a PNA chimera can be a polynucleobase strand wherein the PNA portion of the oligomer is linked to the nucleic acid (NA) portion of the oligomer by a linker. For the avoidance of any doubt, a linked polymer refers to a polymer that comprises a single C-terminus and a single N-terminus.

k. As used herein, the term "alkyl" refers to a straight chained or branched $C_2$-$C_{15}$ hydrocarbon or a cyclic $C_3$-$C_{15}$ hydrocarbon (i.e. a cycloalkyl group such as a cyclopropyl group, a cyclobutyl group, a cyclopentyl group, a cyclohexyl group or a cyclohexylmethylene group) that can be completely saturated. When used herein, the term "alkyl" refers to a group that may be substituted or unsubstituted. When used herein, "alkyl" also refers to an alkyl group wherein one or more of the carbon atoms of a substituted or unsubstituted methylene group may be replaced by a silicon atom (Si). In some embodiments, alkyl groups can be a straight chained or branched $C_2$-$C_{12}$ hydrocarbons or cyclic $C_3$-$C_{10}$ hydrocarbons that can be completely saturated.

l. As used herein, the term "alkylene" refers to a straight or branched alkyl chain or a cyclic alkyl group that has at least two points of attachment to at least two moieties (e.g., —{CH$_2$}— (methylene), —{CH$_2$CH$_2$}—, (ethylene),

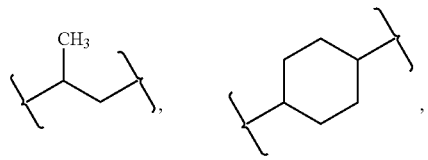

etc., wherein the brackets indicate the points of attachment). When used herein the term "alkylene" refers to a group that may be substituted or unsubstituted. In some embodiments, an alkylene group can be a $C_1$-$C_{10}$ hydrocarbon.

m. As used herein, the term "alkenyl" refers to a straight chained or branched $C_2$-$C_{15}$ hydrocarbon or a cyclic $C_3$-$C_{15}$ hydrocarbon that has one or more double bonds. When used herein, the term "alkenyl" refers to a group that can be substituted or unsubstituted. For the purposes of this specification, "alkenyl" can also refer to an alkenyl group wherein one or more of the carbon atoms of a substituted or unsubstituted methylene group has been replaced by a silicon atom (Si). In some embodiments, alkenyl groups can be straight chained or branched $C_2$-$C_{12}$ hydrocarbons or cyclic $C_3$-$C_{10}$ hydrocarbons that have one or more double bonds.

n. As used herein, the term "alkynyl" refers to a straight chained or branched $C_2$-$C_{15}$ hydrocarbon or a cyclic $C_3$-$C_{15}$ hydrocarbon that has one or more triple bonds. When used herein, the term "alkynyl" refers to a group that can be substituted or unsubstituted. For the purposes of this specification, "alkynyl" can also refer to an alkynyl group wherein one or more of the carbon atoms of a substituted or unsubstituted methylene group has been replaced by a silicon atom (Si). In some embodiments, alkynyl groups can be straight chained or branched $C_2$-$C_{12}$ hydrocarbons or cyclic $C_3$-$C_{10}$ hydrocarbons that have one or more triple bonds.

o. As used herein, the term "heteroalkyl" refers to an alkyl group in which one or more methylene groups in the alkyl chain is replaced by —O— or —S—. When used herein, the term "heteroalkyl" refers to a group that can be substituted or unsubstituted.

p. As used herein, the term "heteroalkenyl" refers to an alkenyl group in which one or more methylene groups is replaced by —O— or —S—. When used herein, the term "heteroalkenyl" refers to a group that can be substituted or unsubstituted.

q. As used herein, the term "heteroalkynyl" refers to an alkynyl group in which one or more methylene groups is replaced by —O— or —S—. When used herein, the term "heteroalkenyl" refers to a group that can be substituted or unsubstituted.

r. As used herein, the term "heterocyclohydrocarbon" refers to a non-aromatic hydrocarbon ring that comprises one or more oxygen and/or sulfur atoms. As used herein, the term "heterocyclohydrocarbon" refers to a group that may be substituted or unsubstituted and/or saturated or unsaturated.

As used herein, the alkyl, alkylene, alkenyl, alkynyl, heteroalkyl, heteroalkenyl, heteroalkynyl, heterocyclohydrocarbon groups do not comprise aromatic substituents. With this exception, suitable substituents for an alkyl, an alkylene, an alkenyl, an alkynyl, a heteroalkyl, a heteroalkenyl, a heteroalkynyl, a heterocyclohydrocarbon group can include any other substituent that is stable under the reaction conditions used in embodiments of this invention. Non-limiting examples of suitable substituents include: an alkyl (e.g., methyl, ethyl, n-propyl, isopropyl, n-butyl, isobutyl, sec butyl, t-butyl, cyclohexyl etc.) group, a haloalkyl (e.g., trifluoromethyl, 2,2,2-trifluoroethyl-) group, an alkoxy (e.g., methoxy, ethoxy, etc.) group, a cyano group or a halo (e.g., fluorine, chlorine, bromine and iodine) group.

s. As used herein, "amino acid" refers to a group represented by R'''—NH—CH(R'''')—C(O)—R''', wherein each R''' is independently hydrogen, an aliphatic group, a substituted aliphatic group, an aromatic group, another amino acid, a peptide or a substituted aromatic group. A "naturally-occurring amino acid" is an amino acid found in nature. These are alanine, valine, leucine, isoleucine, aspartic acid, glutamic acid, serine, threonine, glutamine, asparagine, arginine, lysine, ornithine, proline, hydroxyproline, phenylalanine, tyrosine, tryptophan, cysteine, methionine and histidine. For purposes of interpreting this specification, "a naturally-occurring amino acid" includes naturally occurring amino acids used to indirectly link detectable moieties to the PNA oligomer. In some embodiments, R'''' can be hydrogen or a side-chain of a naturally-occurring amino acid. The naturally occurring amino acid side-chains include methyl (alanine), isopropyl (valine), sec-butyl (isoleucine), —CH$_2$CH(—CH$_3$)$_2$ (leucine), benzyl (phenylalanine), p-hydroxybenzyl (tyrosine), —CH$_2$—OH (serine), —CHOHCH$_3$ (threonine), —CH$_2$-3-indoyl (tryptophan), —CH$_2$COOH (aspartic acid), —CH$_2$CH$_2$COOH (glutamic acid), —CH$_2$C(O)NH$_2$ (asparagine), —CH$_2$CH$_2$C(O)NH$_2$ (glutamine), —CH$_2$SH, (cysteine), —CH$_2$CH$_2$SCH$_3$ (methionine), —(CH$_2$)$_4$NH$_2$ (lysine), —(CH$_2$)$_3$NH$_2$ (ornithine), —{(CH$_2$)$_2$}$_4$NHC(=NH)NH$_2$ (arginine) and —CH$_2$-3-imidazoyl (histidine).

Side-chains of amino acids comprising a heteroatom-containing functional group, e.g., an alcohol (serine, tyrosine, hydroxyproline and threonine), an amine (lysine, ornithine, histidine and arginine), may require a protecting group to facilitate reactions discussed herein (i.e. PNA oligomer synthesis). When the heteroatom-containing functional group is modified to include a protecting group, the side-chain is referred to as the "protected side-chain" of an amino acid. Protecting groups are commonly used in peptide synthesis and these are known to, and often used by, the ordinary practitioner. For example, many suitable protecting groups, and methods for the preparation of protected amino acids, can be found in Green et al., Protecting Groups In Organic Synthesis, Third Edition, John Wiley & Sons, Inc. New York, 1999.

t. As used herein, the term "label refers to any appendage linked to a PNA oligomer. The term "label" includes such terms as "reporter moiety" or "detectable moiety". For the purposes of this specification, a label can also refer to an alkyl group, an alkenyl group, an alkynyl group, a heteroalkyl group, a heteroalkenyl group, a heteroalkynyl group or a heterocyclohydrocarbon group, covalently linked, directly or indirectly, to the N-terminal amine group and/or to the C-terminal carbonyl carbon of a PNA oligomer.

u. As used herein, the terms "reporter moiety" and "detectable moiety" are interchangeable and refer to moieties that can be attached to a polynucleobase strand to thereby render the oligomer detectable by an instrument or method. For example, a label can be any moiety that: (i) provides a detectable signal; (ii) interacts with a second label to modify the detectable signal provided by the first or second label; or (iii) confers a capture function, i.e. hydrophobic affinity, antibody/antigen, ionic complexation.

v. As used herein, "quenching" refers to a decrease in fluorescence of a fluorescent moiety caused by energy transfer associated with a quencher moiety, regardless of the mechanism.

w. As used herein, "support bound" refers to a PNA oligomer immobilized on or to a solid support.

x. As used herein "solid support" or "solid carrier" means any solid phase material upon which a PNA oligomer is synthesized, attached, ligated or otherwise immobilized. Solid support encompasses terms such as "resin", "solid phase", "surface" and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

y. "Array" or "microarray" means a predetermined spatial arrangement of oligomers present on a solid support or in an arrangement of vessels. Certain array formats are referred to as a "chip" or "biochip" (M. Schena, Ed. *Microarray Biochip Technology*, BioTechnique Books, Eaton Publishing, Natick, Mass. (2000). An array can comprise a low-density number of addressable locations, e.g. 2 to about 12, medium-density, e.g. about a hundred or more locations, or a high-density number, e.g. a thousand or more. Typically, the array format is a geometrically-regular shape that allows for fabrication, handling, placement, stacking, reagent introduction, detection, and storage. The array may be configured in a row and column format, with regular spacing between each location. Alternatively, the locations may be bundled, mixed, or homogeneously blended for equalized treatment or sampling. An array may comprise a plurality of addressable locations configured so that each location is spatially addressable for high-throughput handling, robotic delivery, masking, or sampling of reagents, or by detection means including scanning by laser illumination and confocal or deflective light gathering.

5. DESCRIPTION

I. General:

It is to be understood that the discussion set forth below in this "General" section can pertain to some, or to all, of the various embodiments of the invention described herein.

PNA Synthesis:

Methods for the chemical assembly of PNAs are known (See for example: U.S. Pat. Nos. 5,539,082, 5,527,675, 5,623,049, 5,714,331, 5,718,262, 5,736,336, 5,773,571, 5,766,855, 5,786,461, 5,837,459, 5,891,625, 5,972,610, 5,986,053 and 6,107,470). As a general reference for PNA synthesis methodology please see: Nielsen et al., *Peptide Nucleic Acids; Protocols and Applications*, Horizon Scientific Press, Norfolk England (1999).

Figure 2:
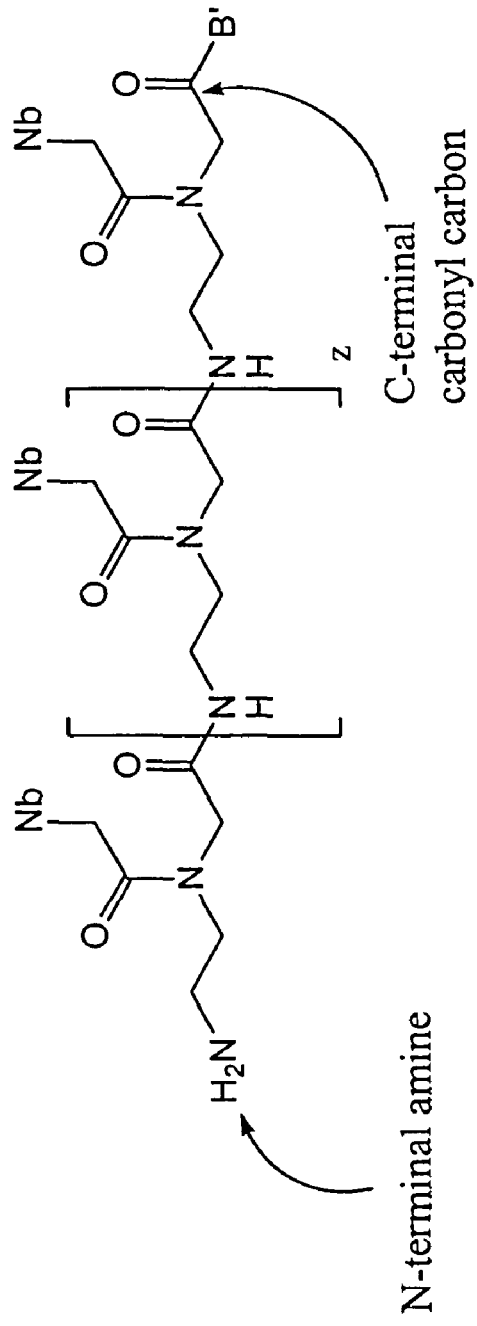
FIG. 2 is an illustration of the general structure of a PNA oligomer identifying the C-terminal carbonyl carbon and the N-terminal amine.

Chemicals and instrumentation for the support bound automated chemical assembly of peptide nucleic acids are available. Both labeled and unlabeled PNA oligomers are available from commercial vendors of custom PNA oligomers. Chemical assembly of a PNA is analogous to solid phase peptide synthesis, wherein at each cycle of assembly the oligomer possesses a reactive alkyl amino terminus that can be condensed with the next synthon to be added to the growing polymer. Because standard peptide chemistry is utilized, natural and non-natural amino acids can be routinely incorporated into a PNA oligomer. Because a PNA is a polyamide, it has a C-terminus (carboxyl terminus) and an N-terminus (amino terminus). The C-terminus can be a C-terminal carboxylic acid or a C-terminal amide, depending on the synthetic methodology chosen for synthesis (See: FIG. 2).

For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide. The orientation of hybridization is not a limitation however, since PNA oligomers are also known to bind in parallel orientation to both nucleic acids and other PNA oligomers.

Figure 3A:
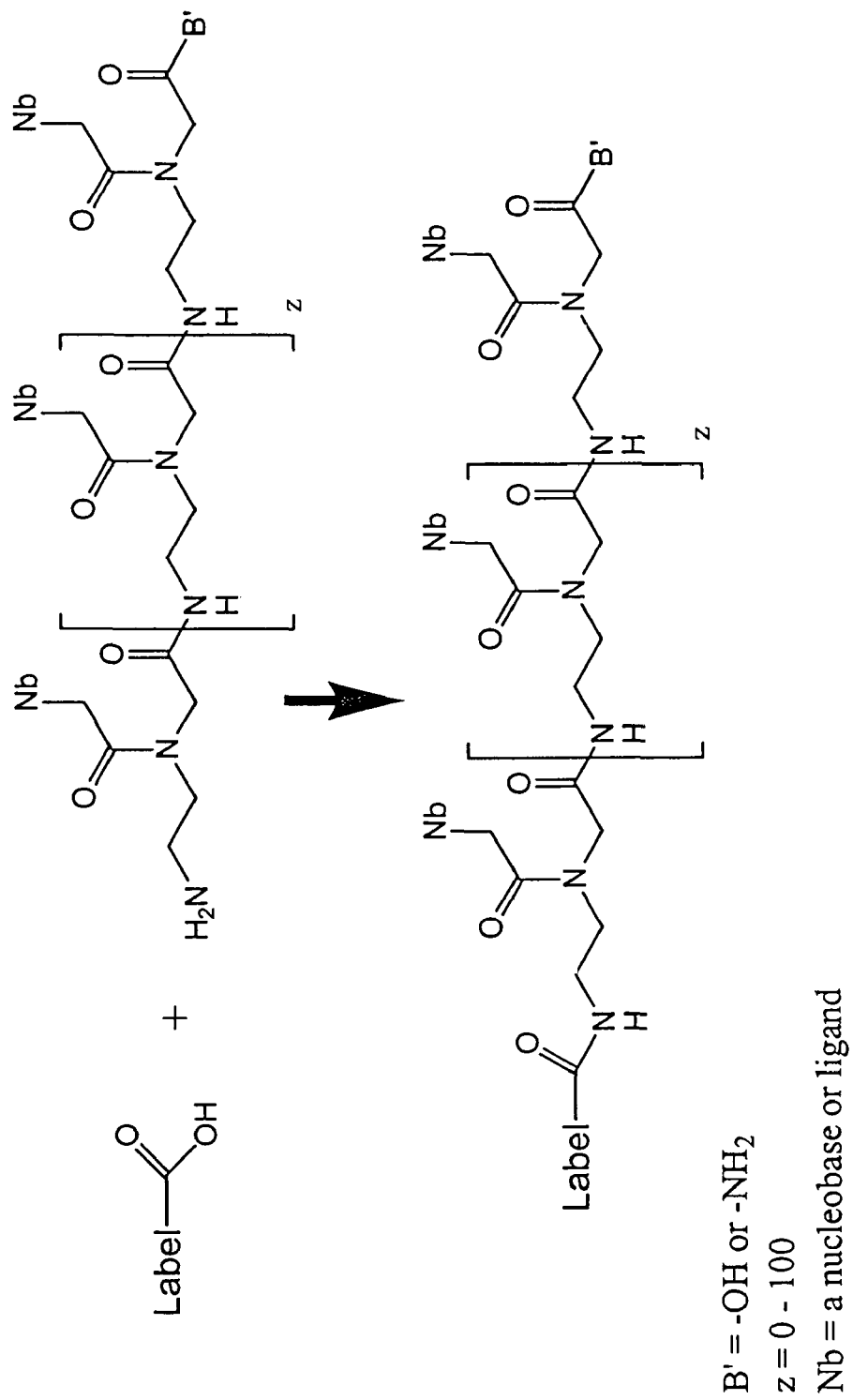
FIG. 3A is an illustration of a condensation reaction whereby the N-terminal amine of the PNA oligomer is condensed with a labeling reagent comprising a carboxylic acid group.
Figure 3B:
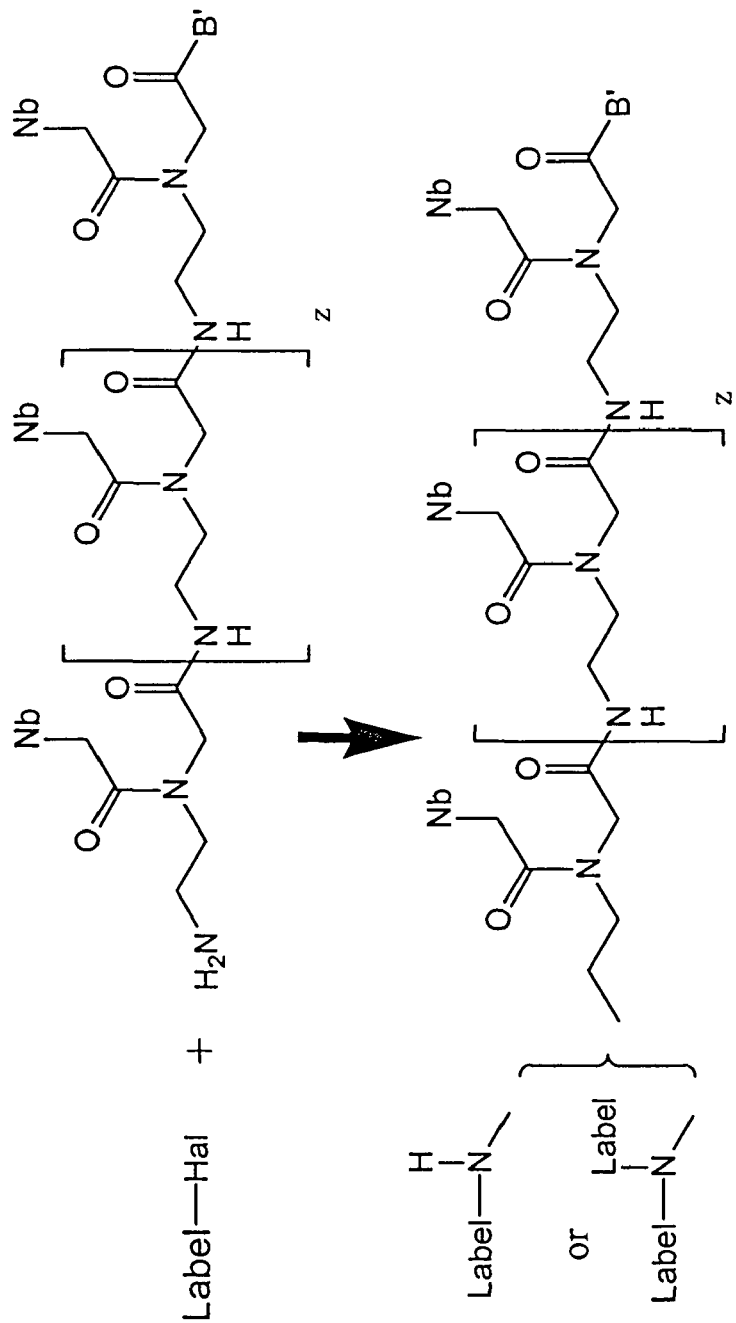
FIG. 3B is an illustration of an alkylation reaction whereby the N-terminal amine is either mono or bis alkylated with a labeling reagent comprising a halogen atom.
Figure 3C:
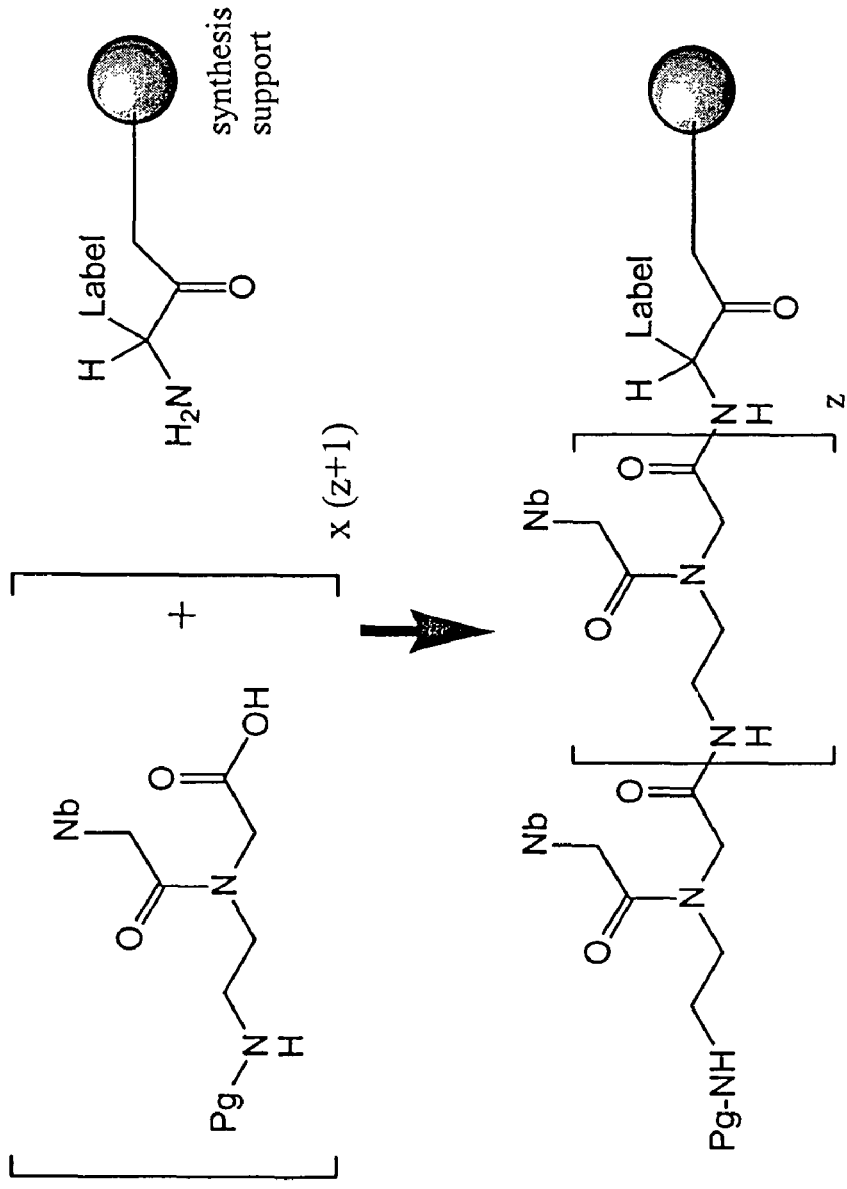
FIG. 3C is an illustration of a method for labeling the C-terminus of an exemplary PNA oligomer by assembly of the PNA oligomer on a synthesis support comprising an amino acid comprising a side chain label (e.g. hydrophobic group).

PNA Labeling:

Non-limiting methods for labeling PNA oligomers are described in U.S. Pat. Nos. 6,110,676, 6,355,421, 6,361,942 and 6,485,901 or are otherwise known in the art of PNA synthesis. Other non-limiting examples for labeling PNA oligomers are also discussed in Nielsen et al., *Peptide Nucleic Acids; Protocols and Applications*, Horizon Scientific Press, Norfolk England (1999). PNA oligomers and oligonucleotides can also be labeled with proteins (e.g. enzymes) and peptides as described in U.S. Pat. No. 6,197,513. Thus, a variety of labeled PNA oligomers can be prepared or purchased from commercial vendors. As used herein, PNA labeling includes covalently linking at least one alkyl group, alkenyl group, alkynyl group, heteroalkyl group, heteroalkenyl group, heteroalkynyl group or heterocyclohydrocarbon group, directly or indirectly, to the N-terminal amine group and/or to the C-terminal carbonyl carbon of a PNA oligomer. Various methods for labeling a PNA are illustrated in FIGS. 3A-3C.

Because the synthetic chemistry of assembly is essentially the same, any method commonly used to label a peptide can often be adapted to effect the labeling a PNA oligomer. Generally, the N-terminus of the polymer can be labeled by reaction with a moiety having a carboxylic acid group or activated carboxylic acid group (FIG. 3A). One or more spacer moieties can optionally be introduced between the labeling moiety and the nucleobase containing subunits of the oligomer. Generally, the spacer moiety can be incorporated prior to performing the labeling reaction. If desired, the spacer may be embedded within the label and thereby be incorporated during the labeling reaction.

The N-terminus can also be modified by alkylation of the amine. Alkylation reactions are well known and can be accomplished by treating an amine with halide of the labeling reagent (e.g. ethyl bromide) under basic conditions (FIG. 3B). Alkylation can proceed such that the amine is twice alkylated. Accordingly, in some embodiments, the amine is monoalkylated and in some embodiments the amine is bis alkylated.

The C-terminal end of the polymer can be labeled by first condensing a labeled moiety or functional group moiety with the support upon which the PNA oligomer is to be assembled (For example see: FIG. 3C). Next, the first nucleobase containing synthon of the PNA oligomer can be condensed with the labeled moiety or functional group moiety. Alternatively, one or more spacer moieties (e.g. 8-amino-3,6-dioxaoctanoic acid; the "O-linker") can be introduced between the label moiety or functional group moiety and the first nucleobase subunit of the oligomer. Once the molecule to be prepared is completely assembled by repetitive momomer additions, N-terminally labeled and/or modified, it can be cleaved from the support deprotected and purified using standard methodologies.

By still another method, the label can be attached to the PNA oligomer after it is fully assembled and cleaved from the support. This method can be applied where the label is incompatible with the cleavage, deprotection or purification regimes commonly used to manufacture the oligomer. The labeling can proceed generally as illustrated in FIG. 3A-3C except that the labeling reaction takes place in solution and not while the PNA oligomer is support bound. By this method, the PNA oligomer can be labeled in solution by the reaction of a functional group on the polymer and a functional group on the label.

Those of ordinary skill in the art will recognize that the composition of the coupling solution will depend on the nature of oligomer and label, such as for example a donor or acceptor moiety. The solution may comprise organic solvent, water or any combination thereof. Generally, the organic solvent will be a polar non-nucleophilic solvent. Non limiting examples of suitable organic solvents include acetonitrile (ACN), tetrahydrofuran, dioxane, methyl sulfoxide, N,N'-dimethylformamide (DMF) and N-methylpyrrolidone (NMP).

The functional group on the polymer to be labeled can be a nucleophile (e.g. an amino group such as the N-terminal amine) and the functional group on the label can be an electrophile (e.g. a carboxylic acid or activated carboxylic acid (i.e. a C-terminal carboxylic acid). It is however contemplated that this can be inverted such that the functional group on the polymer can be an electrophile (e.g. a carboxylic acid or activated carboxylic acid) and the functional group on the label can be a nucleophile (e.g. an amino acid group). Non-limiting examples of activated carboxylic acid functional groups include N-hydroxysuccinimidyl esters. In aqueous solutions, the carboxylic acid group of either of the PNA or label (depending on the nature of the components chosen) can be activated with a water soluble carbodiimide. The reagent, 1-ethyl-3-(3-dimethylaminopropyl)carbodiimide hydrochloride (EDC), is a commercially available reagent sold specifically for aqueous amide forming condensation reactions. Applicants have likewise observed that such condensation reactions can be improved when 1-Hydroxy-7-azabenzotriazole (HOAt) or 1-hydrozybenzotriazole (HOBt) is mixed with the EDC.

The pH of aqueous solutions can be modulated with a buffer during the condensation reaction. For example, the pH during the condensation can be in the range of about 4 to about 10. Generally, the basicity of non-aqueous reactions can be modulated by the addition of non-nucleophilic organic bases. Non-limiting examples of suitable bases include N-methylmorpholine, triethylamine and N,N-diisopropylethylamine. Alternatively, the pH can be modulated using biological buffers such as (N-[2-hydroxyethyl]piperazine-N'-[2-ethanesulfonic acid) (HEPES) or 4-morpholineethanesulfonic acid (MES) or inorganic buffers such as sodium bicarbonate.

Nucleic Acid Synthesis and Modification

Nucleic acid oligomer (oligonucleotide and oligoribonucleotide) synthesis has been routine for many years. For a detailed description of nucleic acid synthesis please see Gait, M. J., *Oligonucleotide Synthesis: a Practical Approach*. IRL Press, Oxford England. Those of ordinary skill in the art will recognize that both labeled and unlabeled oligonucleotides (DNA, RNA and synthetic analogues thereof) are readily available. They can be synthesized using commercially available instrumentation and reagents or they can be purchased from commercial vendors of custom manufactured oligonucleotides.

PNA Chimera Synthesis and Modification:

PNA chimeras are a combination of nucleic acid and peptide nucleic acid subunits. A suitable reference for the synthesis, labeling and modification of PNA chimeras can be found in U.S. Pat. No. 6,063,569. Moreover, the methods described above for PNA synthesis and labeling often can be used to modify the PNA portion of a PNA chimera. Additionally, known methods for the synthesis and labeling of nucleic acids can often be used to modify the nucleic acid portion of a PNA chimera. Hence, the synthesis, labeling and modification of PNA chimeras can utilize methods known to those of skill in the art as well as those described, or made reference to, above.

Labels:

PNA oligomers (including PNA chimeras) can comprise at least one detectable moiety. Non-limiting examples of detectable moieties that can be used to label polynucleobase strands (e.g. PNA oligomers) include a dextran conjugate, a branched nucleic acid detection system, a chromophore, a fluorophore, a spin label, a radioisotope, an enzyme, a hapten, an acridinium ester or a chemiluminescent compound. Other suitable labeling reagents and preferred methods of attachment would be recognized by those of ordinary skill in the art of PNA, peptide or nucleic acid synthesis.

Non-limiting examples of haptens include 5(6)-carboxyfluorescein, 2,4-dinitrophenyl, digoxigenin, and biotin.

Non-limiting examples of fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Non-limiting examples of enzymes include polymerases (e.g. Taq polymerase, Klenow DNA polymerase, T7 DNA polymerase, Sequenase, DNA polymerase 1 and phi29 polymerase), alkaline phosphatase (AP), horseradish peroxidase (HRP), soy bean peroxidase (SBP)), ribonuclease and protease.

Spacer/Linker Moieties:

PNA oligomers (including PNA chimeras) can comprise a spacer and/or linker moiety. Generally, spacers are used to minimize the adverse effects that bulky labeling reagents might have on hybridization properties of probes. Linkers typically induce flexibility and randomness into the polynucleobase strand or otherwise link two or more nucleobase sequences of a polynucleobase strand. Preferred spacer/linker moieties for the polynucleobase strands described herein can comprise one or more aminoalkyl carboxylic acids (e.g. aminocaproic acid), the side chain of an amino acid (e.g. the side chain of lysine or ornithine), natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties can also incidentally or intentionally be constructed to improve the water solubility of the polynucleobase strand (For example see: Gildea et al., *Tett. Lett.* 39: 7255-7258 (1998) and U.S. Pat. Nos. 6,326,479 and 6,770,442).

For example, a spacer/linker moiety can comprise one or more linked compounds having the formula: -Q-($O_m$—($CM_2$)$_n$)$_o$-T-. The group Q can be selected from the group consisting of: a single bond, —($CM_2$)$_p$—, —C(O)($CM_2$)$_p$—, —C(S)($CM_2$)$_p$— and —S($O_2$)($CM_2$)$_p$—. The group T can have the formula NH, NR'''', S, —$SO_2$— or O. Each M can be independently H, R'''', —O R'''', F, Cl, Br or I; wherein, each R'''' can be independently selected from the group consisting of: —$CV_3$, —$CV_2CV_3$, —$CV_2CV_2CV_3$, —$CV_2CV(CV_3)_2$ and —$C(CV_3)_3$, wherein each V can be independently hydrogen (H), fluorine (F), chlorine (Cl), bromine (Br) or iodine (I). Each m can be independently 0 or 1. Each n, o and p can be independently integers from 0 to 10. In some embodiments, each n, o and p can be independently integers from 0 to 3.

Energy Transfer

Energy transfer can be used in hybridization analysis. For energy transfer to be useful in determining hybridization, there should be an energy transfer set comprising at least one energy transfer donor and at least one energy transfer acceptor moiety. For example, a self-indicating PNA oligomer can be labeled in a manner that is described in U.S. Pat. Nos. 6,326,479, 6,355,421 or 6,485,901. Often, the energy transfer set will include a single donor moiety and a single acceptor moiety, but this is not a limitation. An energy transfer set may contain more than one donor moiety and/or more than one acceptor moiety. The donor and acceptor moieties operate such that one or more acceptor moieties accepts energy transferred from the one or more donor moieties or otherwise quenches the signal from the donor moiety or moieties. Thus, in some embodiments, both the donor moiety(ies) and acceptor moiety(ies) are fluorophores. Though the previously listed fluorophores (with suitable spectral properties) might also operate as energy transfer acceptors the acceptor moiety can also be a quencher moiety such as 4-((4-(dimethylamino)phenyl)azo) benzoic acid (dabcyl). The labels of the energy transfer set can be linked at the oligomer block termini or linked at a site within the PNA oligomer. In one embodiment, each of two labels of an energy transfer set can be linked at the distal-most termini of the PNA oligomer. PNA oligomers comprising donor and acceptor moieties can also comprise at least one linked amino acid that comprises a charged group at physiological pH.

Transfer of energy between donor and acceptor moieties may occur through any energy transfer process, such as through the collision of the closely associated moieties of an energy transfer set(s) or through a non-radiative process such as fluorescence resonance energy transfer (FRET). For FRET to occur, transfer of energy between donor and acceptor moieties of a energy transfer set requires that the moieties be close in space and that the emission spectrum of a donor(s) have substantial overlap with the absorption spectrum of the acceptor(s) (See: Yaron et al. *Analytical Biochemistry*, 95: 228-235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228-235 (1979) and particularly page 229, col. 1 through page 232, col. 1). This process is referred to as intramolecular collision since it is believed that quenching is caused by the direct contact of the donor and acceptor moieties (See: Yaron et al.). It is to be understood that any reference to energy transfer in the instant application encompasses all of these mechanistically-distinct phenomena. It is also to be understood that energy transfer can occur though more than one energy transfer process simultaneously and that the change in detectable signal can be a measure of the activity of two or more energy transfer processes. It is to be understood that energy transfer can also occur by mechanisms that have not been described. Accordingly, the mechanism of energy transfer is not a limitation of this invention.

Figure 4A:
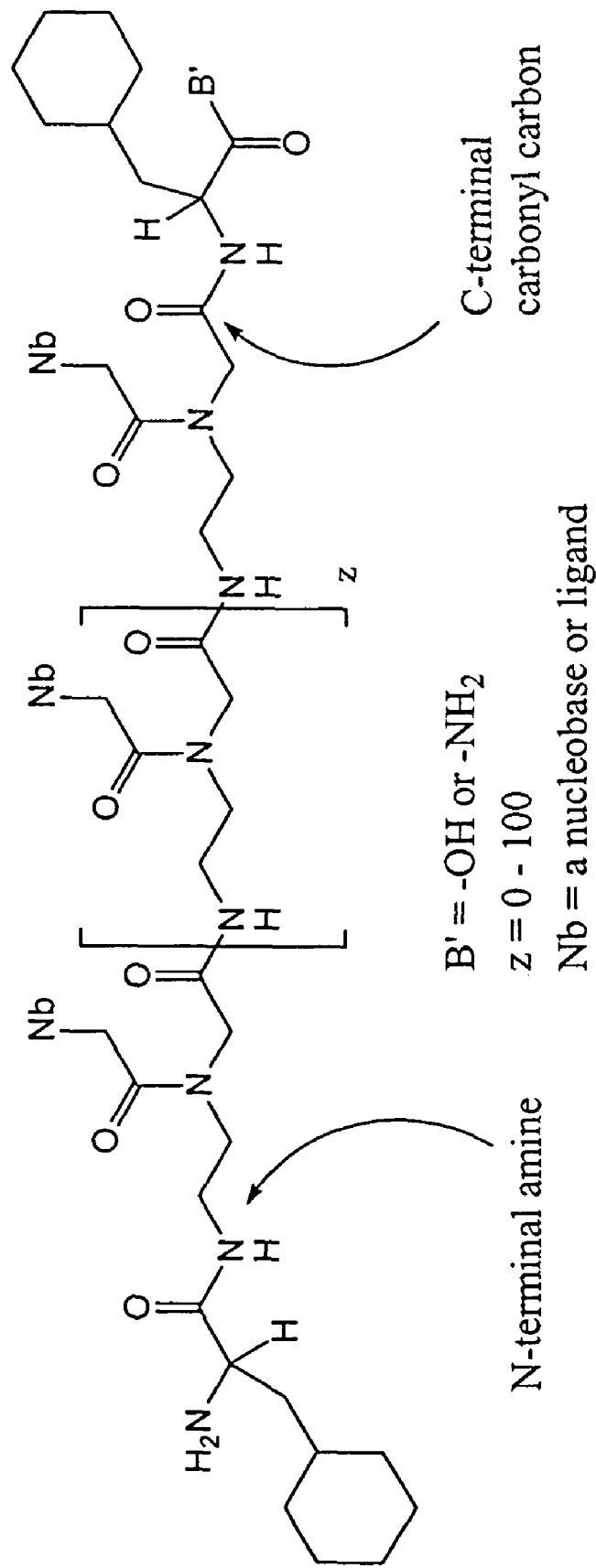
FIG. 4A is an illustration of an embodiment of a bis labeled PNA oligomer.

Detecting Energy Transfer in a Self-Indicating PNA Oligomer:

In some embodiments, the PNA oligomers are self-indicating. For example, a self-indicating PNA oligomer can be labeled in a manner that is described in U.S. Pat. Nos. 6,326,479, 6,355,421 or 6,485,901. Various examples of self-indicating polymers can be found in FIGS. 4C-4F. As can be seen by the figures, various placements are possible for the hydrophobic groups, energy acceptor moieties and energy acceptor moieties. In some embodiments, amino acids comprising charge groups can also be added (FIG. 4F). These charged groups can form salt bridges that stabilize the unhybridized oligomer is a certain conformation. As can be seen from the various figures, the energy donor and energy acceptor moieties can be on either end but typically are on opposite ends of the PNA oligomer.

Hybrid formation between a self-indicating PNA oligomer and a polynucleobase strand can be monitored by measuring at least one physical property of at least one member of the energy transfer set that is detectably different when the PNA oligomer/NA complex is formed as compared with when the PNA oligomer exists in a non-hybridized state. We refer to this phenomenon as the self-indicating property of the PNA oligomer. This change in detectable signal results from the change in efficiency of energy transfer between donor and acceptor moieties caused by hybridization of the PNA oligomer to the nucleic acid sequence.

For example, the means of detection can involve measuring fluorescence of a donor or acceptor fluorophore of an energy transfer set. For example, the energy transfer set may comprise at least one donor fluorophore and at least one acceptor (fluorescent or non-fluorescent) quencher such that the measure of fluorescence of the donor fluorophore can be used to detect, identify and/or quantify hybridization of the PNA oligomer to the nucleic acid.

In some embodiments, the energy transfer set comprises at least one donor fluorophore and at least one acceptor fluorophore such that the measure of fluorescence of either, or both, of at least one donor moiety or one acceptor moiety can be used to detect, identify and/or quantify hybridization of the PNA oligomer to the nucleic acid.

Detectable and Independently Detectable Moieties/Multiplex Analysis:

In some embodiments, a multiplex hybridization assay is performed. In a multiplex assay, numerous conditions of interest are simultaneously or sequentially examined. Multiplex analysis relies on the ability to sort sample components or the data associated therewith, during or after the assay is completed. In performing a multiplex assay, one or more distinct independently detectable moieties can be used to label two or more different PNA oligomers that are used in an assay. By independently detectable we mean that it is possible to determine one detectable moiety independently of, and in the presence of, the other detectable moiety. The ability to differentiate between and/or quantify each of the independently detectable moieties provides the means to multiplex a hybridization assay because the data correlates with the hybridization of each of the distinct, independently labeled PNA oligomer to a particular target sequence sought to be determined in the sample. Consequently, the multiplex assays can, for example, be used to simultaneously and/or sequentially detect the presence, absence, number, position and/or identity of two or more target sequences in the same sample and in the same assay.

II. Various Embodiments of the Invention:

Applicants have discovered that covalently linking, directly or indirectly, one or more alkyl groups, alkenyl groups, alkynyl groups, heteroalkyl groups, heteroalkenyl groups, heteroalkynyl groups and/or heterocyclohydrocarbon groups to the N-terminal amine group and/or to the C-terminal carbonyl carbon of a PNA oligomer can significantly raise the $T_m$ of the PNA oligomer/NA complex. The increase in thermal stability ($T_m$) of a PNA oligomer/nucleic acid complex (PNA oligomer/NA complex) depends on the nature, number and position of the group or groups that are linked. Accordingly, the $T_m$ of the complex can be modulated depending upon the nature, number and position of the groups that are linked to the PNA oligomer.

The increase in $T_m$ does not seem to be substantially dependent on the sequence of the PNA oligomer. Therefore, linking the same substituent in the same location on two or more different PNA oligomers of same length should raise the $T_m$ of the complex formed between the PNA oligomer and its complementary polynucleobase strand by approximately the same number of ° C. Accordingly, individual PNA oligomers, sets of PNA oligomers and/or libraries of PNA oligomers can be prepared whereby the $T_m$ of the PNA oligomers for complementary polynucleobase strands can be modulated (e.g. increased) in a substantially predictable manner.

In some embodiments, Applicants have observed an increase in $T_m$, for the modified PNA oligomer/NA complex compared to the unmodified PNA oligomer/NA complex, that is in excess of 10° C. (See: Example 2 and the Table). Therefore, it is possible that 8-mer and/or 9-mer libraries could be constructed, with or without the inclusion of universal nucleobases, that might be useful for large scale genetic analysis projects as well as for use in other probe-based assay formats.

a. Compositions:

Accordingly, in some embodiments, this invention pertains to PNA oligomers comprising an N-terminal amine group and a C-terminal carbonyl carbon and further comprising at least one alkyl group, alkenyl group, alkynyl group, heteroalkyl group, heteroalkenyl group, heteroalkynyl group or heterocyclohydrocarbon group covalently linked, directly or indirectly, to the N-terminal amine group and/or to the C-terminal carbonyl carbon provided that the group is not an acetyl group or a side chain of a terminally linked natural amino acid. In some embodiments, the group can comprise a substituted or unsubstituted cyclic hydrocarbon. For example, each group can comprise a substituted or unsubstituted cyclopropyl, cyclobutyl, cyclopentyl or cyclohexyl group. For the avoidance of any doubt, when we refer to linked groups (whether directly or indirectly), we do not mean a group that is integral to the PNA oligomer (e.g. a component of the PNA backbone structure or a ligand linked to a nitrogen, other than to the N-terminal amine, of the PNA backbone) such as a PNA subunit comprising a cyclohexyl group (e.g. Lagriffoule et al., *Chem. Eur. J.* 3(6): 912-919 (1997)).

In some embodiments, one or more of the following provisos may also apply. In some embodiments, each group is not a steroid. In some embodiments, each group is uncharged at physiological pH. In some embodiments, each group does not comprise a basic nitrogen at physiological pH. In some embodiments, each group is linked directly to the N-terminal amine group and/or to the C-terminal carbonyl carbon (e.g. the group is not associated with a linked amino acid residue). In some embodiments, the group is not a linker used to link the PNA oligomer to a solid support.

In some embodiments, one or more of the groups is indirectly linked to the N-terminal amine group and/or to the C-terminal carbonyl carbon (See FIGS. 3A-4F). For example, the linked group or groups can be the side chain of an unnatural amino acid such as β-cyclohexyl alanine (e.g. FIGS. 4A, 4C, 4D, 4E & 4F). In this embodiment, the group is cyclohexylmethylene. Non-limiting examples of some suitable groups have the formula:

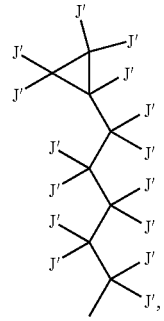

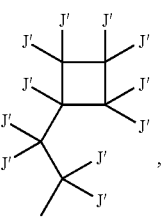

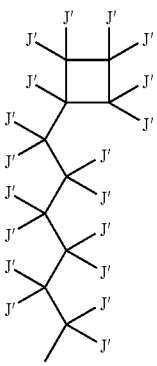

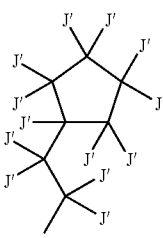

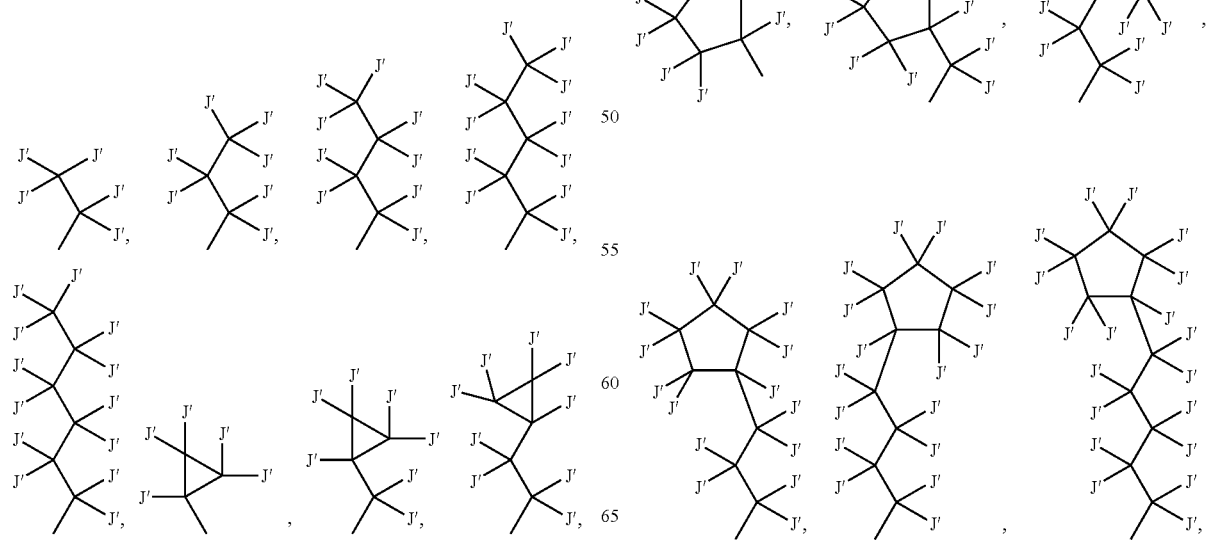

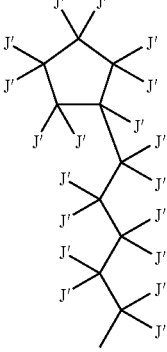

-continued

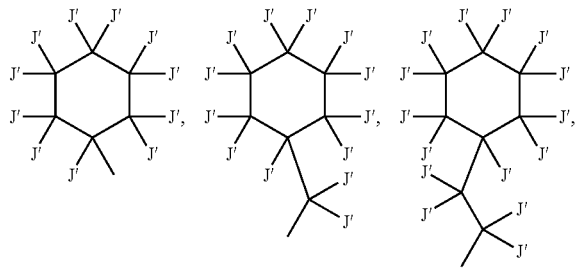

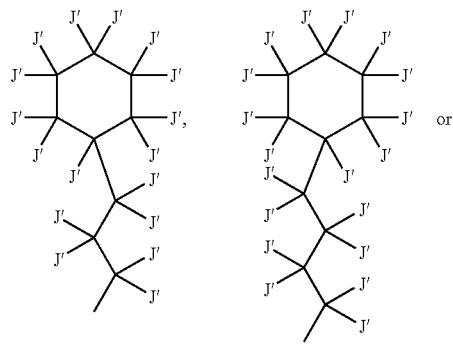

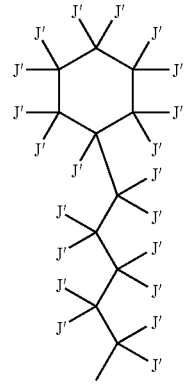

wherein each J' is independently H, F, Cl, Br, I, —OH, —SH, —CX₃, —SCX₃ or —OCX₃ and wherein each X is independently H, F, Cl, Br or I. With reference to the structures set forth immediately above, in some embodiments, one or more moieties of the formula C(J')₂ in the group can optionally be substituted with a moiety of the formula: C=O, C=S, S or O and/or wherein one or more of the moieties of the formula:

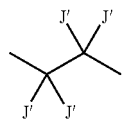

in the group can optionally be substituted with a moiety of the formula:

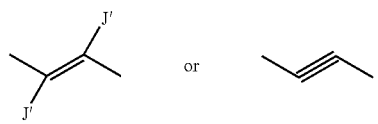

provided that the group is not aromatic when substituted and further provided that the group does not have the formula:

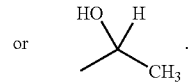

Figure 4B:
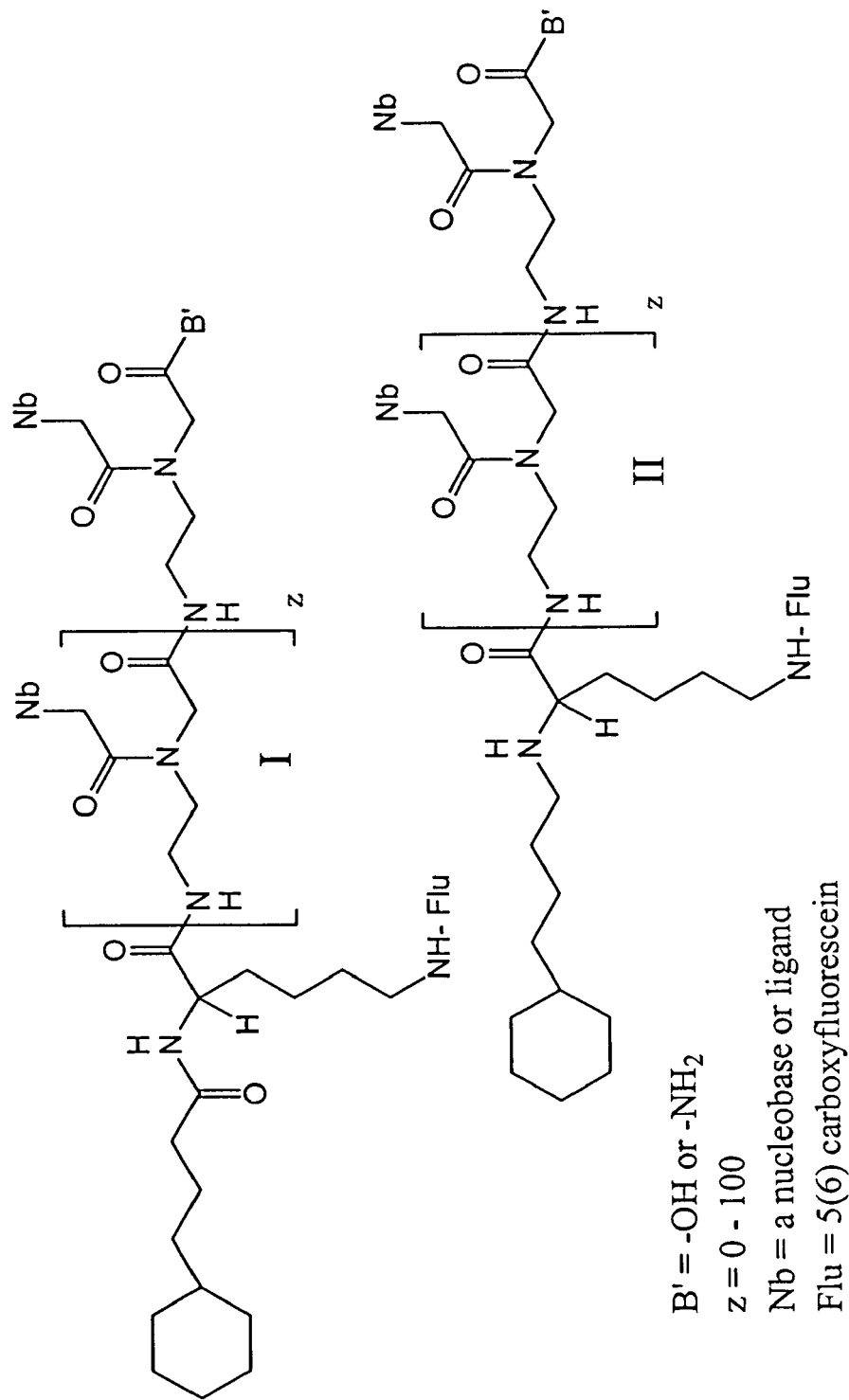
FIG. 4B is an illustration an embodiment of two PNA oligomers each comprising an N-terminal hydrophobic group and a detectable moiety.
Figure 4C:
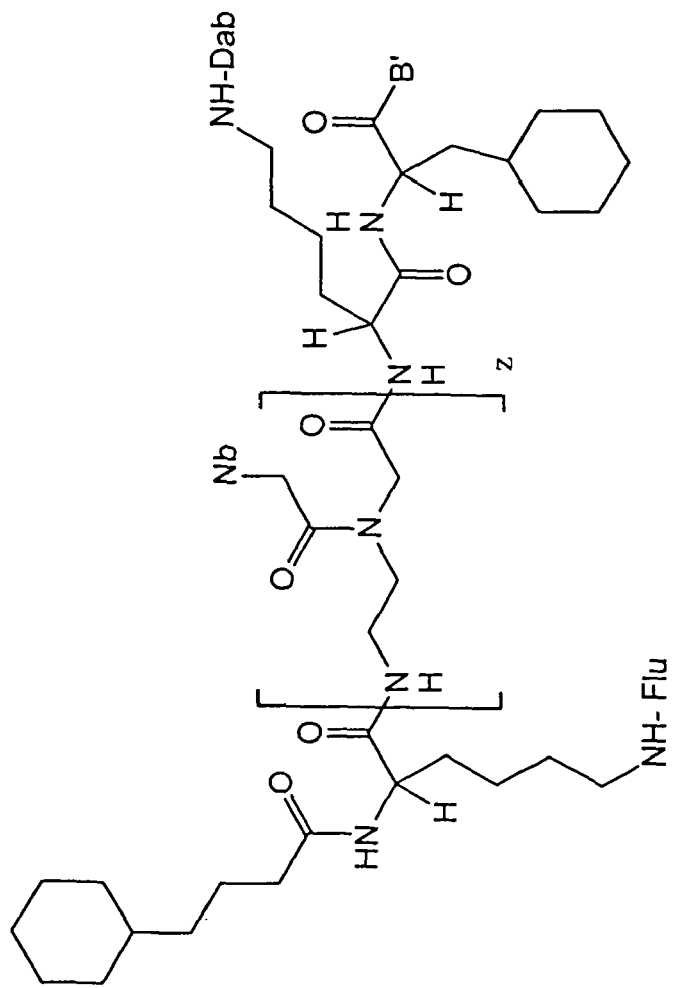
FIG. 4C is an illustration of an embodiment of a PNA oligomer comprising two hydrophobic groups, an energy donor moiety and an energy acceptor moiety
Figure 4D:
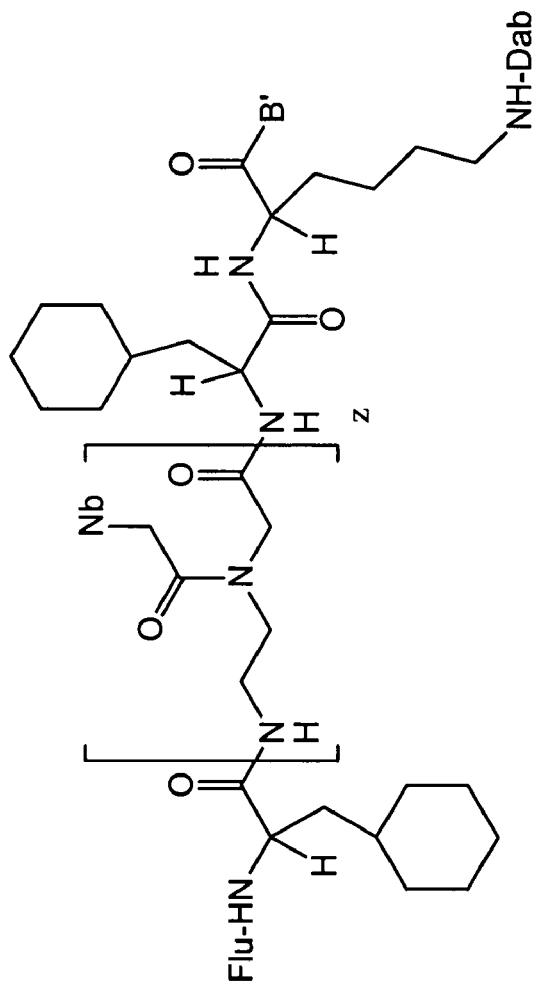
FIG. 4D is an illustration of another embodiment of a PNA oligomer comprising two hydrophobic groups, an energy donor moiety and an energy acceptor moiety.
Figure 4E:
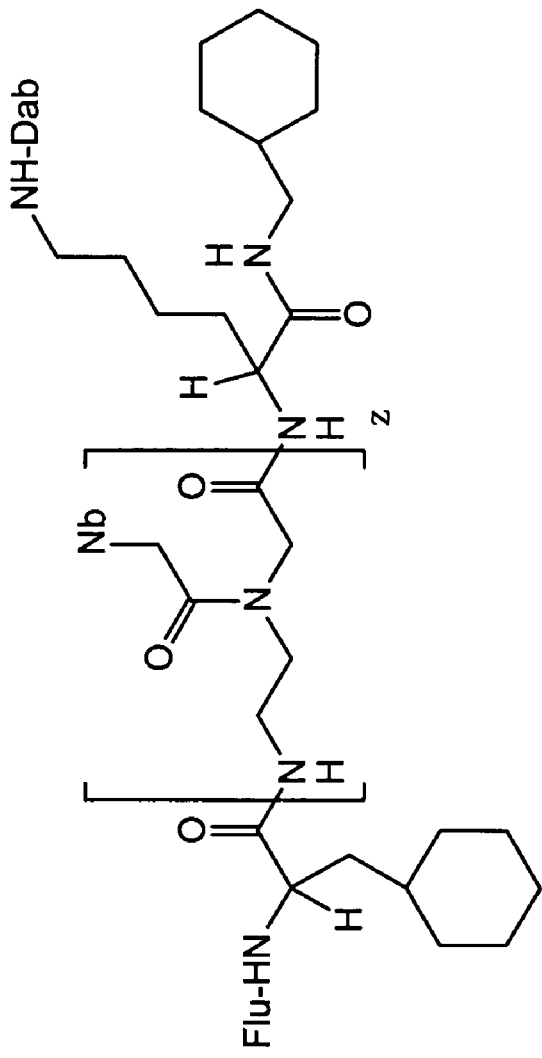
FIG. 4E is an illustration of yet another embodiment of a PNA oligomer comprising two hydrophobic groups, an energy donor moiety and an energy acceptor moiety.
Figure 4F:
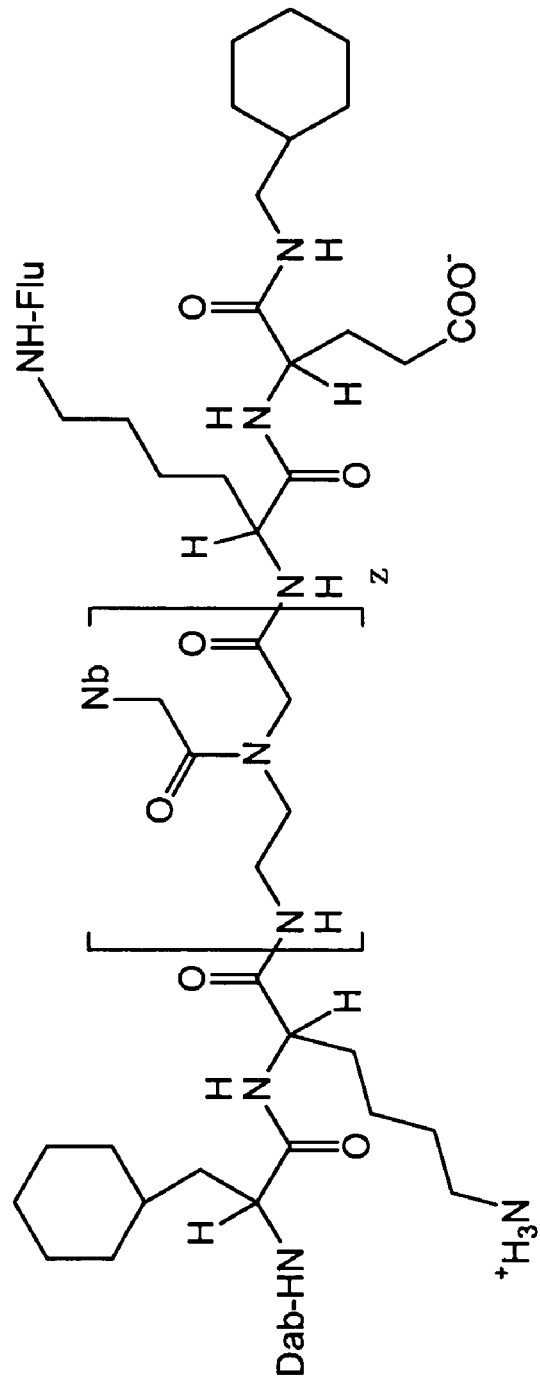
FIG. 4F is an illustration of an embodiment of a PNA oligomer comprising two hydrophobic groups, two charged amino acids, an energy donor moiety and an energy acceptor moiety.

In some embodiments, the PNA oligomer comprises one or more of said above described groups linked directly to the N-terminal amine (e.g. FIGS. 3B & 4B (cpds. I and II). These groups can be directly linked to the terminal amine by direct alkylation of said amine.

In some embodiments, the group that is directly or indirectly linked to the N-terminal amine can have the formula:

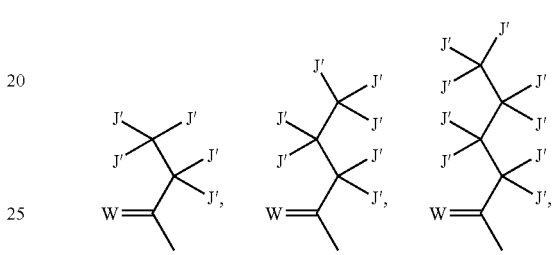

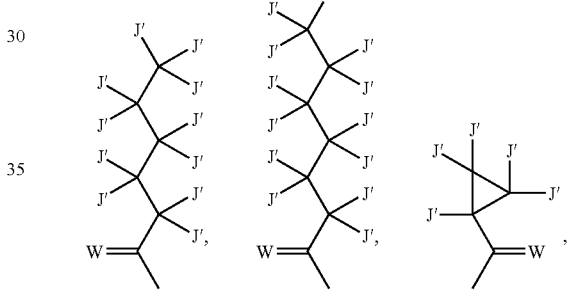

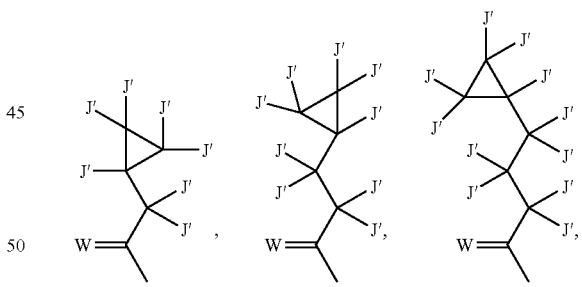

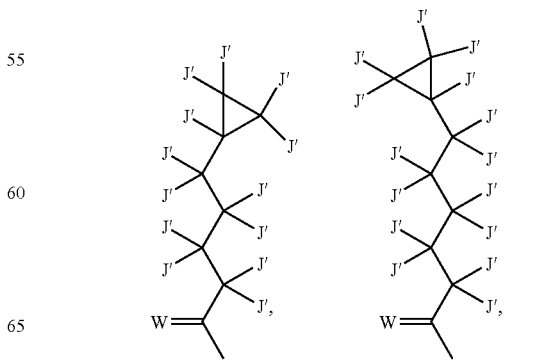

-continued

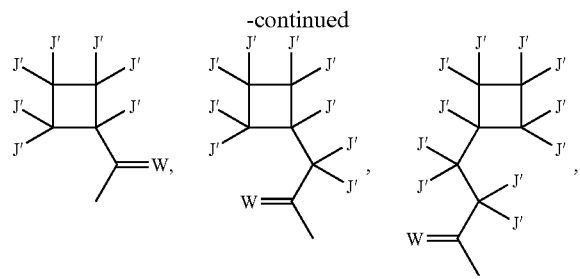

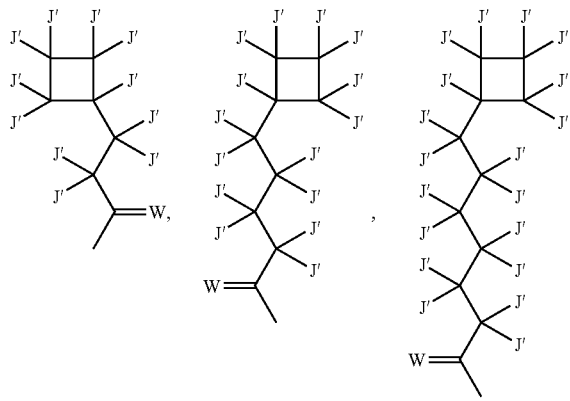

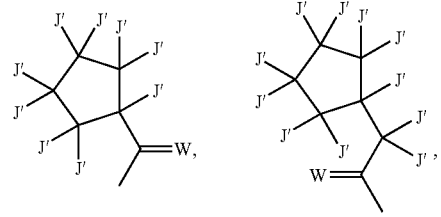

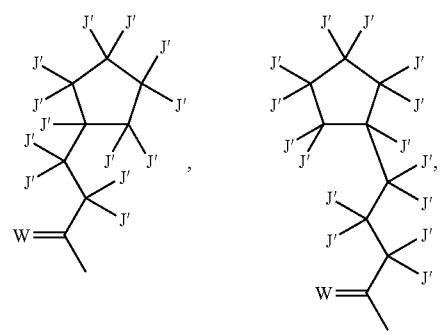

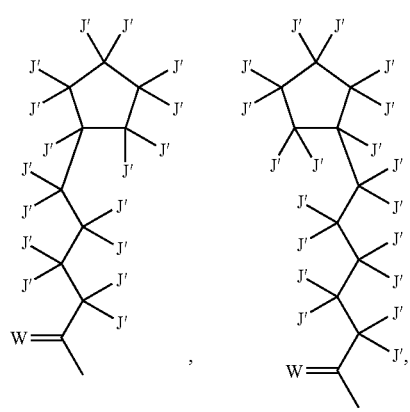

-continued

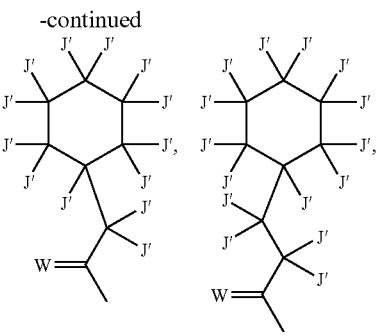

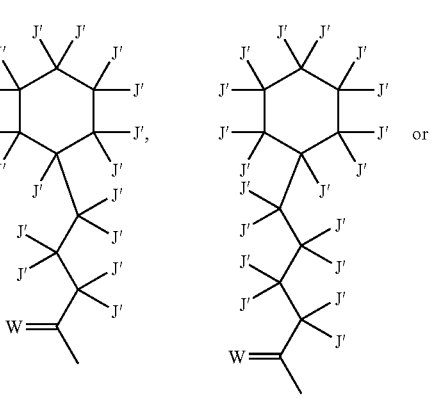

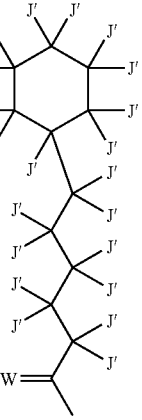

wherein, each J' is independently H, F, Cl, Br, I, —OH, —SH, —CX$_3$, —SCX$_3$ or —OCX$_3$, wherein each X is independently H, F, Cl, Br or I; and wherein W is O or S (e.g. FIGS. 3A, 4A, 4B (cpd. I) & 4D). With reference to the structures set forth immediately above, in some embodiments, one or more moieties of the formula C(J')$_2$ in the group can optionally be substituted with a moiety of the formula: C=O, C=S, S or O and/or wherein one or more of the moieties of the formula:

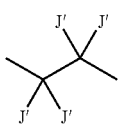

in the group can optionally be substituted with a moiety of the formula:

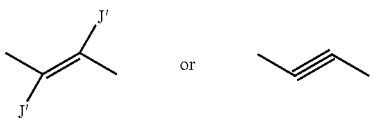

provided that the group is not aromatic when substituted.

Figure 3D:
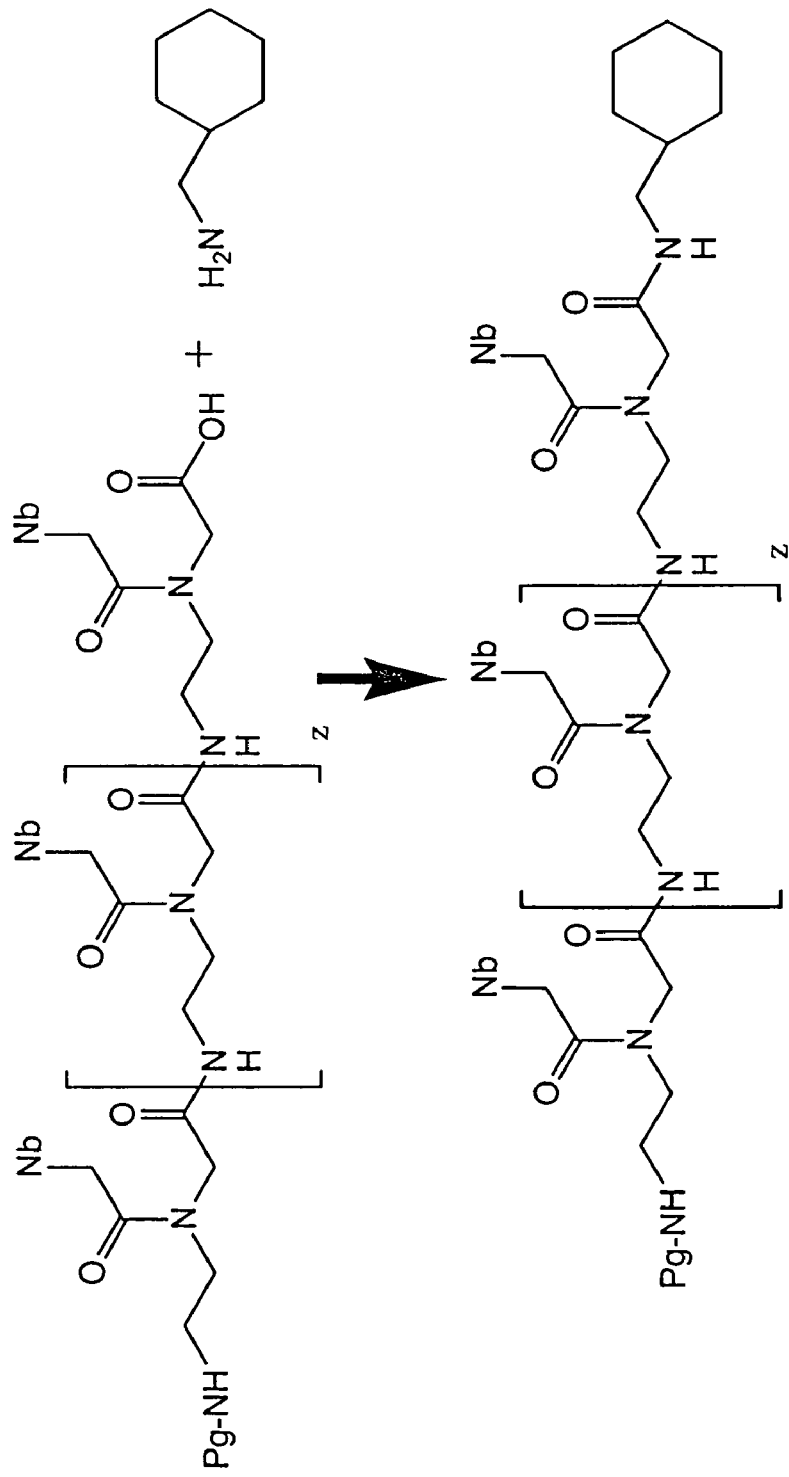
FIG. 3D is an illustration of a condensation reaction whereby the C-terminal carbonyl carbon is reacted with a hydrophobic labeling reagent comprising an amine group.

In some embodiments, the PNA oligomer can comprise a C-terminal carboxylic acid group. In some embodiments, the C-terminal carboxylic acid group can be, if desired, used to ligate a PNA oligomer to thereby form a combination oligomer (See: US Patent Application Publication No. 2003-0077608), it can be used to immobilize the PNA oligomer to a support or it can be used to link a label (e.g. a group) to the PNA oligomer (FIG. 3D).

In some embodiments, the PNA oligomer comprises one or more groups linked directly to the C-terminal carbonyl carbon (e.g. FIGS. 3D, 3E, 4E & 4F). For example, the group that is directly linked to the C-terminal carbonyl carbon can have the formula:

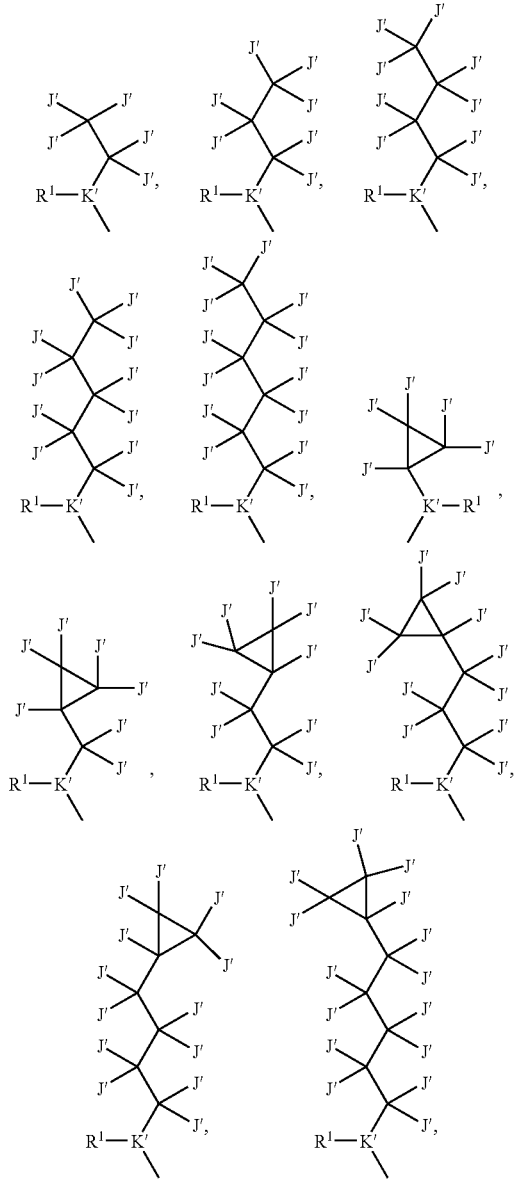

-continued

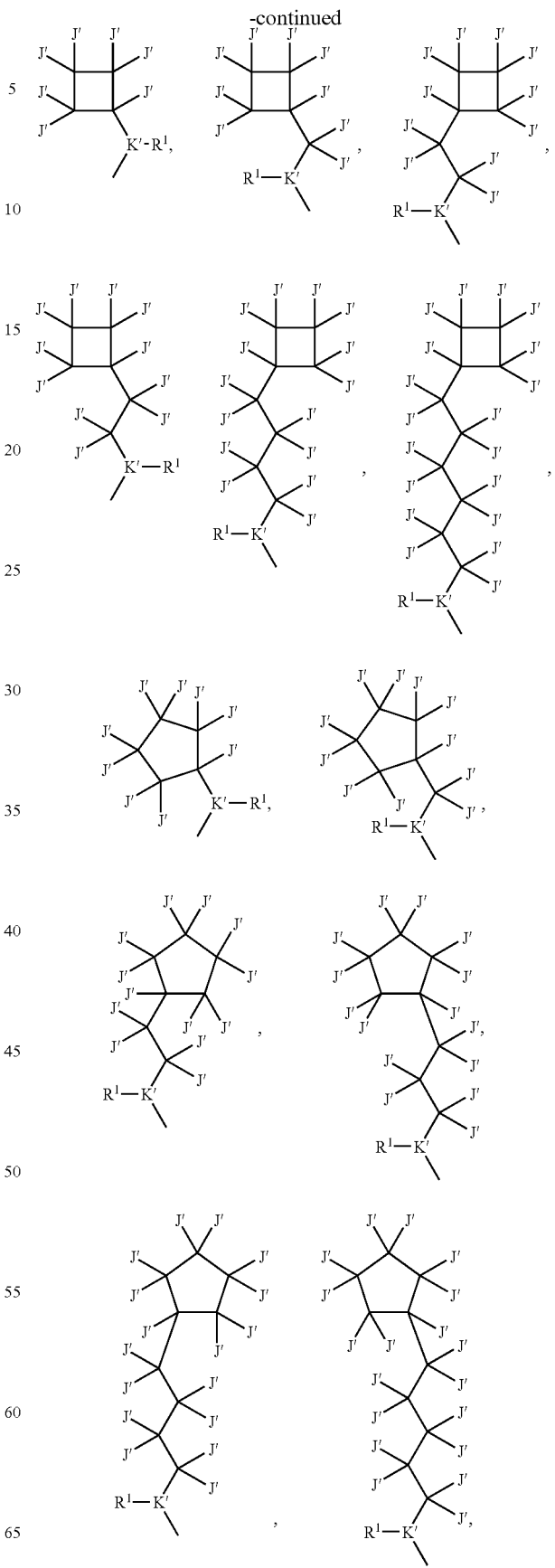

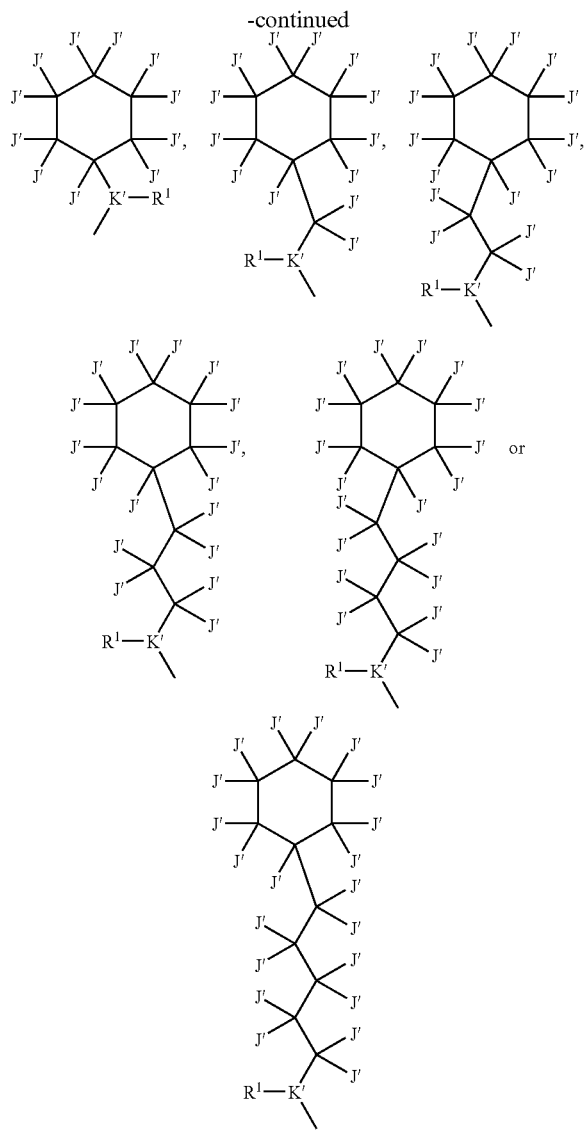

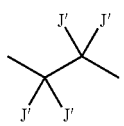

wherein, K' is N, O or S, each J' is independently H, F, Cl, Br, I, —OH, —SH, —CX$_3$, —SCX$_3$ or —OCX$_3$, wherein each X is independently H, F, Cl, Br or I; and wherein if K' is O or S, R$^1$ is nothing (i.e. there is no group covalently linked to K') but if K' is N then R$^1$ is hydrogen or an alkyl group, alkenyl group, alkynyl group, heteroalkyl group, heteroalkenyl group, heteroalkynyl group or heterocyclohydrocarbon group. With reference to the structures set forth immediately above, in some embodiments, one or more moieties of the formula C(J')$_2$ in the group can optionally be substituted with a moiety of the formula: C═O, C═S, S or O and/or wherein one or more of the moieties of the formula:

in the group can optionally be substituted with a moiety of the formula:

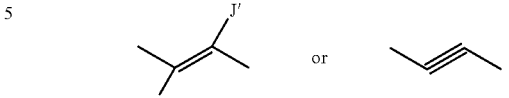

provided that the group is not aromatic when substituted.

As stated, in some embodiments, the group or groups are linked to the N-terminal amine, in some embodiments, the group or groups are linked to the C-terminal carbonyl carbon and in some embodiments, the group or groups are linked to both the N-terminal amine and to the C-terminal carbonyl carbon. In some embodiments, two or more of the same or different groups are linked to the N-terminal amine. In some embodiments, two or more of the same or different groups are linked to the C-terminal carbonyl carbon. In some embodiments, two or more of the same or different groups are linked to each of the N-terminal amine and the C-terminal carbonyl carbon. The groups can be linked directly or indirectly. The groups can be linked in addition to other moieties such one or more detectable moieties. When other moieties are present, the various groups and moieties can be linked at various positions (e.g. FIGS. 4A-4F).

In some embodiments, the PNA oligomer can further comprise at least one detectable moiety (e.g. FIG. 4B). In some embodiments, the PNA oligomer can further comprise at least one energy donor moiety and at least one energy acceptor moiety (e.g. FIGS. 4C-4F). Probes comprising at least one energy donor moiety and at least one energy acceptor moiety can be self-indicating and can be used in real-time and end-point based hybridization analysis and in multiplex hybridization assays (e.g. See U.S. Pat. Nos. 6,355,421 and 6,485,901).

In some embodiments, the PNA oligomer can further comprise at least one natural amino acid comprising a charged group at physiological pH. For example, the PNA oligomer can comprise one or more amino acids comprising an acidic side chain (e.g. a carboxylic acid group) and/or one or more amino acids comprising a basic side chain (e.g. an amine) (e.g. FIG. 4F). In some embodiments, the PNA oligomer can comprise at least one universal nucleobase (e.g. FIG. 1B). In some embodiments, the PNA oligomer can comprise at least one diaminopurine nucleobase (e.g. FIG. 1B).

In some embodiments, the PNA oligomer is a PNA chimera comprising one or more linked C-terminal nucleosides or nucleotides. PNA chimeras comprising one or more linked C-terminal nucleosides or nucleotides can be extended by a polymerase (See: U.S. Pat. No. 6,316,230). Accordingly, they can be used in various types of genetic analysis such as DNA sequencing, DNA fragment analysis, reverse transcription, mini-sequencing, chromosome labeling, amplification and single nucleotide polymorphism (SNP) detection.

In some embodiments, a library of two or more PNA oligomer can be prepared. For example a library of 8-mer or 9-mer PNA oligomers can be prepared wherein the PNA oligomers comprise an N-terminal amine group and a C-terminal carbonyl carbon and further comprise at least one alkyl group, alkenyl group, alkynyl group, heteroalkyl group, heteroalkenyl group, heteroalkynyl group or heterocyclohydrocarbon group covalently linked, directly or indirectly, to the N-terminal amine group and/or to the C-terminal carbonyl carbon provided that the group is not an acetyl group or a side chain of a terminally linked natural amino acid.

In some embodiments, the PNA oligomers of the libraries can be used as probes and/or primers in hybridization assays. In some embodiments, the PNA oligomers of the libraries can be used in ligation reactions to thereby produce longer PNA oligomers that can be used as probes and/or primers in hybridization assays (e.g. see US Patent Application Publication No. 2003-0077608).

Figure 3E:
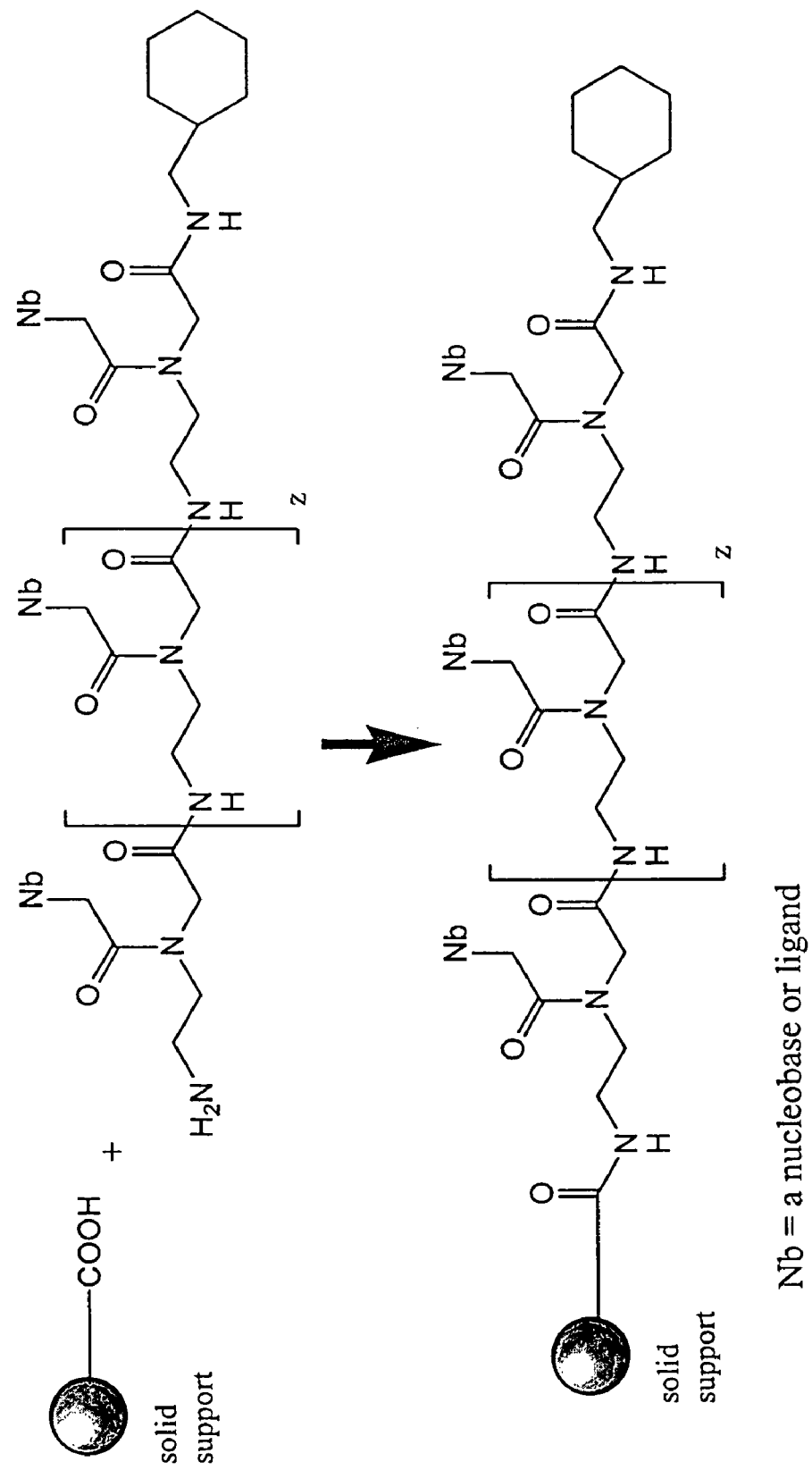
FIG. 3E is an illustration of a condensation reaction whereby the N-terminal amine of a PNA oligomer comprising a C-terminal hydrophobic group is covalently immobilized to a solid support.
Figure 6:
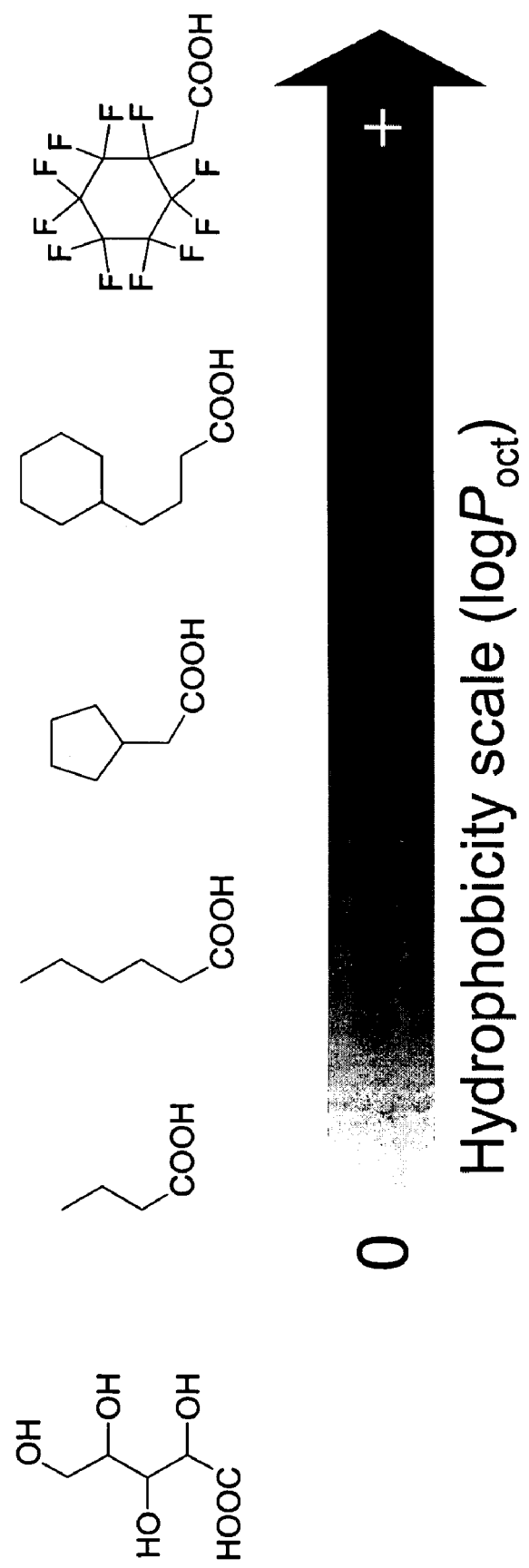
FIG. 6 is an illustration of various groups that can be linked to the N-terminal amine or C-terminal carbonyl carbon of a PNA oligomer as well as their relative hydrophobicity on the logP$_{oct}$ scale.

In some embodiments, the PNA oligomer described herein can be linked to a solid support (e.g. FIG. 3E). In some embodiments, one or more PNA oligomers described herein can be used to form an array. Support bound PNA oligomers can be used as probes and/or primers in hybridization assays.

b. Methods:

Applicants observed that the melting temperature ($T_m$) of PNA oligomer/NA complexes increases in relation to the hydrophobicity of N-terminally linked groups. The linking of groups to both the C-terminus and the N-terminus further increase the $T_m$. The increase in $T_m$ is substantially independent of the sequence of the participating oligonucleotides and depends largely on the hydrophobicity, as measured by the $logP_{oct}$ (i.e. the partition coefficient of the compound in octanol-water extraction), of the N-terminally linked group. FIG. 6 illustrates various possible groups that can be linked to the PNA oligomer and their relation on the $logP_{oct}$ scale. Accordingly, the increase in $T_m$ is dependent upon the nature, number and position of the groups linked to the PNA oligomer. Moreover, the presence of other groups, such as fluorophores and charged moieties, can also influence (i.e. increase or decrease) the $T_m$ of the complex formed by the PNA oligomer and a complementary polynucleobase strand thereby possibly marginalizing the influence of appended hydrophobic groups.

In essence, linking the alkyl group, alkenyl group, alkynyl group, heteroalkyl group, heteroalkenyl group, heteroalkynyl group or heterocyclohydrocarbon group to the PNA oligomer is analogous to labeling. PNA oligomers described in the section entitled "Compositions", above, can be produced by covalently linking the one or more groups to the PNA oligomer by applying standard synthetic procedures used for labeling (For example see the section entitled "PNA Labeling", above) and the appropriately modified group. For example, the N-terminus can be reacted with an amino acid, alkylated or reacted with a group comprising an activated carboxylic acid.

Accordingly, in some embodiments, this invention also pertains to forming a PNA oligomer comprising an N-terminal amine group and a C-terminal carbonyl carbon and further comprising least one alkyl group, alkenyl group, alkynyl group, heteroalkyl group, heteroalkenyl group, heteroalkynyl group or heterocyclohydrocarbon group covalently linked, directly or indirectly, to the N-terminal amine group and/or to the C-terminal carbonyl carbon, provided that the group is not an acetyl group or a side chain of a terminally linked natural amino acid.

The PNA oligomer compositions described above can be used as probes and/or primers in hybridization assays. The PNA probes/primers can hybridize to complementary polynucleobase strands to thereby form a complex. For example, the PNA probes/primers can hybridize to a nucleic acid to thereby form a PNA oligomer/NA complex. Accordingly, this invention also pertains to a method comprising forming a PNA oligomer/NA complex wherein the PNA oligomer comprises an N-terminal amine group and a C-terminal carbonyl carbon and further comprises least one alkyl group, alkenyl group, alkynyl group, heteroalkyl group, heteroalkenyl group, heteroalkynyl group or heterocyclohydrocarbon group covalently linked, directly or indirectly, to the N-terminal amine group and/or to the C-terminal carbonyl carbon, provided that the group is not an acetyl group or a side chain of a terminally linked natural amino acid.

As discussed previously, the nature, number and position of groups linked to a PNA oligomer will affect the $T_m$ of the complex formed with a polynucleobase strand as compared with the complex formed from the unmodified PNA oligomer. Applicants have observed that the effect on modulation of the $T_m$ appears to be substantially independent of the nucleobase sequence of the PNA oligomer. According it is possible to modulate the $T_m$ of the PNA oligomer in a predicable manner by judiciously choosing the one or more groups to be linked to the PNA oligomer provided one has obtained basic information about how the various groups affect the $T_m$. Such information can be generated by routine experimentation. For example, various forms of modified PNA oligomers can be prepared and the $T_m$s determined. Because the modulation of $T_m$ is substantially independent of the nucleobase sequence, it is possible to use the information derived from controlled experiments to reasonably predict the effect the presence of one or more groups will have on the $T_m$ of various other PNA oligomers modified in accordance with those for which experimental data has been obtained.

Accordingly, this invention further pertains to a method comprising modulating the $T_m$ of a PNA oligomer/NA complex in a substantially predictable manner by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid. By "substantially predictable" we mean predictable to within +/−1-2° C.

c. Kits:

In some embodiments, this invention also pertains to a kit comprising a PNA oligomer comprising an N-terminal amine group and a C-terminal carbonyl carbon and further comprising at least one alkyl group, alkenyl group, alkynyl group, heteroalkyl group, heteroalkenyl group, heteroalkynyl group or heterocyclohydrocarbon group covalently linked, directly or indirectly, to the N-terminal amine group and/or to the C-terminal carbonyl carbon of the PNA oligomer, provided that the group is not an acetyl group or a side chain of a terminally linked natural amino acid.

Said kits can be designed for specific hybridization assays. For example, the kit can be designed for PCR analysis. Such a PCR kit could comprise the PNA oligomer and other reagents, mixtures and/or compositions selected to perform a PCR assay. For example the kit could comprise a polymerase enzyme and nucleotide triphosphates. If the kit was to be used for sequencing, it might further comprise dideoxy terminators.

6. EXAMPLES

Aspects of the present teachings can be further understood in light of the following examples, which should not be construed as limiting the scope of the present teachings in any way.

Example 1

Figure 5:
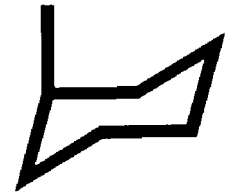
FIG. 5 is an illustration of two PNA oligomers each comprising either an acetyl group or a cyclohexylbutryl group.

Two PNAs were synthesized to validate that the concept of $T_m$ modulation could be applied to PNA oligomers. One PNA oligomer was acetylated (Compound III, FIG. 5) and the second cyclohexyl butrylated (Compound IV, FIG. 5). PNA oligomers have long been acetyl capped so the PNA oligomer comprising the acetyl group was chosen as a control. Modulation of $T_m$ as compared with the control was measured to determine the effect associated with the longer alkyl group.

Synthesis of the PNA oligomers was accomplished using standard Fmoc protocol on an Expedite PNA synthesizer. Modification of the N-terminus (acetyl or cyclohexyl butryl group addition) was performed while the PNA oligomer was still support bound. In both cases the PNA oligomer was reacted with either acetic anhydride (to produce Compound III) or cyclohexylbutyric acid in combination with O-(7-azabenzotriazol-1-yl)-N,N,N',N'-tetramethyluronium hexafluorophosphate (HATU) (to produce Compound IV). Both PNAs were obtained in high purity using C-18 reverse phase HPLC purification methods.

Melting temperature study of these two PNAs demonstrated that there is a 7-8° C. increase in $T_m$ of the cyclohexylbutyryl modified PNA over the acetylated PNA.

Example 2

In an additional experiment, several PNA oligomers were prepared and their $T_m$s compared. For this example, the PNA oligomer was either C-terminally modified, N-terminally modified or both C-terminally and N-terminally modified. To accomplish the modification, the amino acid Fmoc-β-cyclohexyl-Ala-OH (393.5 g/mol, L# 522434, Bachem P/N B1975) was used on the Expedite synthesizer as a monomer. Thus, the amino acid could be incorporated into the C-terminus, the N-terminus or both the C-terminus and the N-terminus (See the Table) simply by coupling the amino acid during the PNA oligomer assembly. Addition of this amino acid introduces a cyclohexyl methylene group at various positions in the PNA oligomer.

TABLE

| SEQ ID NO | Sequence | MW | $T_m$ | Difference |
|---|---|---|---|---|
| 1 | GTA-TCC-AAG-T-ChAla | 2878.9 | 42.91 | +0.89 |
| 2 | ChAla-GTA-TCC-AAG-T-ChAla | 3033.1 | 52.22 | +10.21 |
| 3 | ChAla-GTA-TCC-AAG-T | 2879.9 | 50.91 | +8.9 |
| 4 | GTA-TCC-AAG-T (control) | 2726.6 | 42.01 | 0.0 |

ChAla = β-cyclohexyl-Ala

With reference to the data in the Table, it can be seen that $T_m$ modulation differs substantially depending on whether the group is linked to the C-terminus or the N-terminus (See entries 1 and 3). However, if both of the termini comprise the group, there is an additive effect such that, in this case, the net increase in $T_m$ exceeds 10° C. Thus, from the data it is clear that it is possible to achieve large increases in $T_m$ depending on the nature, number and position of groups added to the PNA oligomer. With appropriate evaluation of the $T_m$ of various groups in various positions, it should be possible to modulate the $T_m$ of a PNA oligomer/NA complex, in a substantially predictable manner, by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid.

While the present teachings are described in conjunction with various embodiments, it is not intended that the present teachings be limited to such embodiments. On the contrary, the present teachings encompass various alternatives, modifications and equivalents, as will be appreciated by those of skill in the art.

7. REFERENCES

1. Bleczinski et al., *JACS* 121: 10889-10894 (1999)
2. Challa et al., *Organic Letters*, 1 (10): 1639-1641 (1999)
3. Coull et al., US Patent Application Publication No. 2003-0077608
4. Garner et al., *Chembiochem*, 3: 224-226 (2001)
5. Gryazpnov et al., *Nucl. Acids. Res.* 21: 5909-5915 (1993)
6. Guckian et al., *JACS*, 122: 2213-2222 (2000)
7. Kohler et al., *ChemBioChem*, 6: 69-77 (2005)
8. Letsinger et al., *Proceedings of the National Academy of Sciences* USA, 86: 6553-6556 (1998)
9. Lagriffoule et al., *Chem. Eur. J.*, 3(6): 912-919 (1997)
10. Nielsen et al., WO98/03542
11. Petersheim et al., *Biochemistry*, 22: 256-263 (1983)
12. Seela et al. *Nucl. Acids Res.*, 28(17): 3224-3232 (2000)
13. Senior et al., *Biochemistry*, 27: 3879-3885 (1988)
14. Zhang et al., *Methods*, 23: 132-140 (2001)

We claim:

1. A method comprising modulating the $T_m$ of a PNA oligomer/NA complex, comprising covalently linking, directly or indirectly, to the PNA oligomer, comprising an N-terminal amine group and a C-terminal carbonyl carbon, at least one modifying moiety selected from an alkyl group, an alkenyl group, an alkynyl group, a heteroalkyl group, a heteroalkenyl group, a heteroalkynyl group and a heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, to thereby obtain a PNA oligomer/NA complex having the $T_m$ that is higher by at least 10 degrees than a $T_m$ of a corresponding PNA oligomer/NA complex that does not have the modifying moiety covalently linked thereto.

2. The method of claim 1, wherein each alkyl, alkenyl, alkynyl, heteroalkyl, heteroalkenyl, heteroalkynyl or heterocyclohydrocarbon group is uncharged at physiological pH.

3. The method of claim 1, wherein each group comprises a substituted or unsubstituted cyclic hydrocarbon group.

4. The method of claim 3, wherein each cyclic hydrocarbon group is a substituted or unsubstituted cyclopropyl, cyclobutyl, cyclopentyl or cyclohexyl group.

5. The method of claim 1, wherein each group does not comprise a basic nitrogen at physiological pH.

6. The method of claim 1, wherein each group is indirectly linked to the N-terminal amine group and/or to the C-terminal carbonyl carbon.

7. The method of claim 6, wherein each indirectly linked group is the side chain of a non-naturally occurring amino acid.

8. The method of claim 1, wherein each group is linked directly to the N-terminal amine group.

9. The method of claim 1, wherein each group is linked directly to the C-terminal carbonyl carbon.

10. The method of claim 1, wherein a different group is linked to each of the C-terminus and the N-terminus.

11. The method of claim 1, wherein the same group is linked to each of the C-terminus and the N-terminus.

12. The method of claim 8, wherein each group independently has the formula:

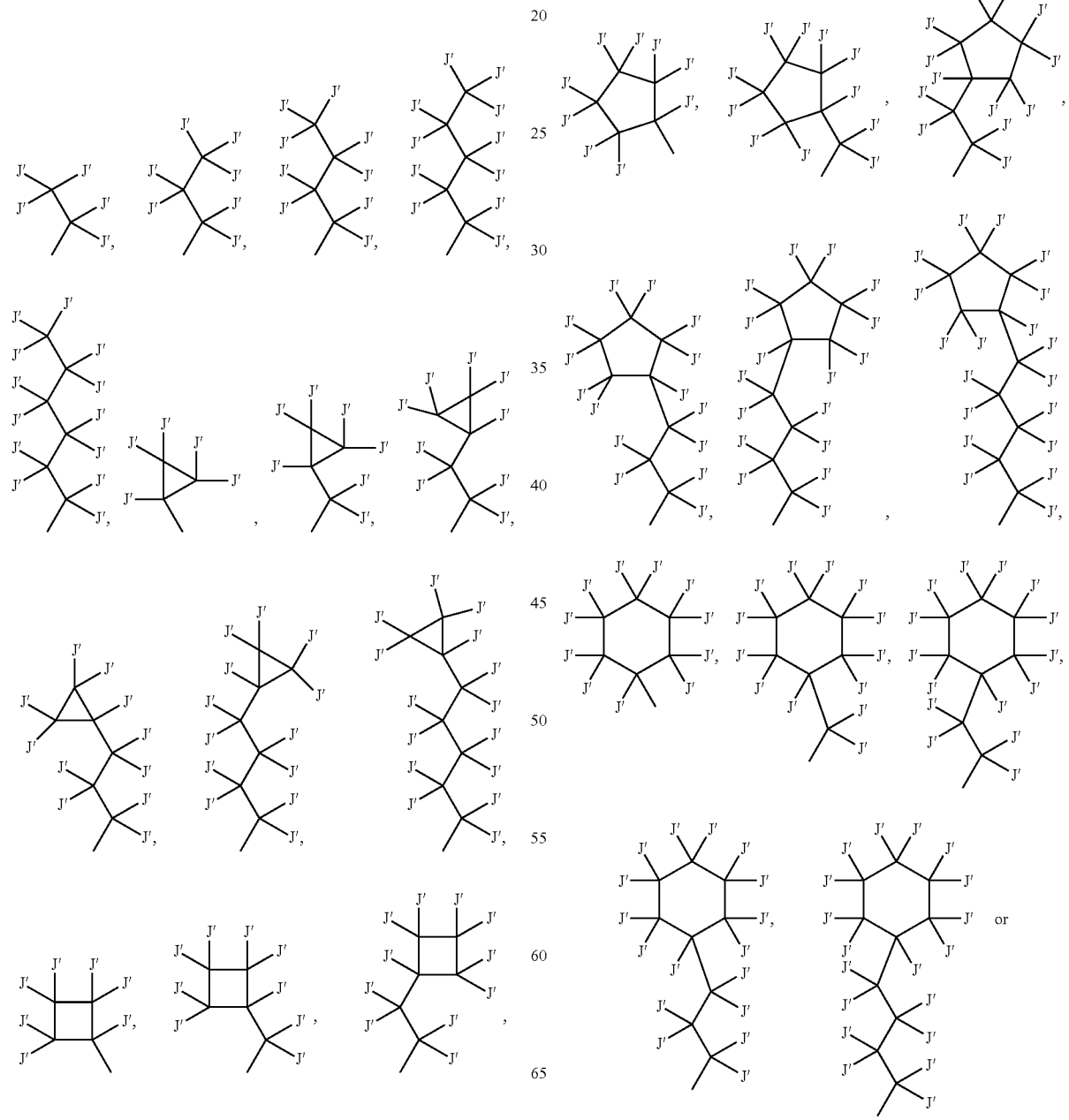

-continued

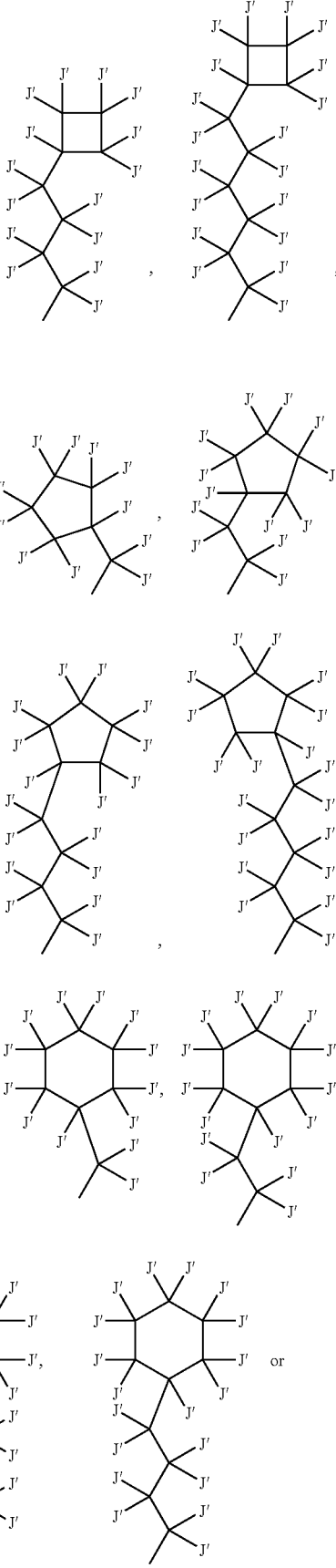

-continued

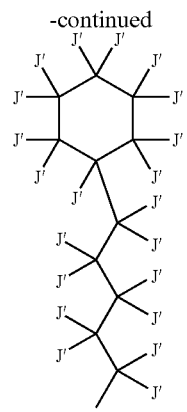

wherein each J' is independently H, F, Cl, Br, I, —OH, —SH, —CX$_3$, —SCX$_3$ or —OCX$_3$ wherein each X is independently H, F, Cl, Br or I.

13. The method of claim 12, wherein one or more moieties of the formula C(J')$_2$ in the group is optionally substituted with a moiety of the formula: C=O, C=S, S or O and/or wherein one or more of the moieties of the formula:

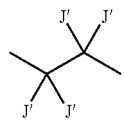

in the group is optionally substituted with a moiety of the formula:

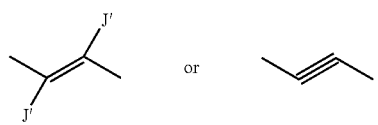

provided that the group is not aromatic when substituted and further provided that the group does not have the formula:

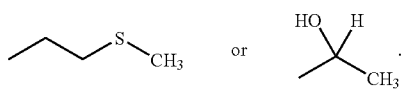

14. The method of claim 8, wherein each group independently has the formula:

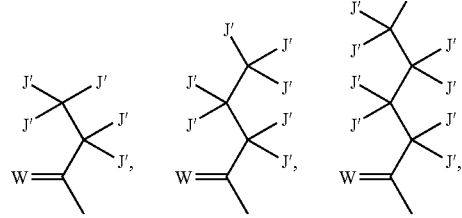

-continued

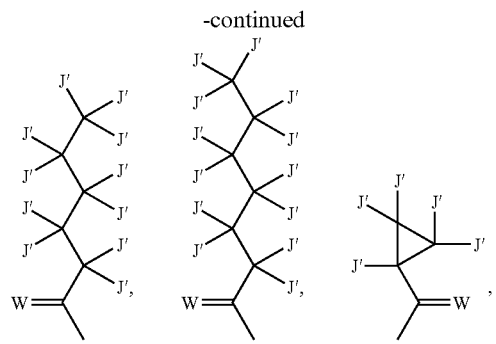

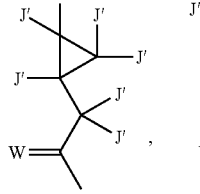
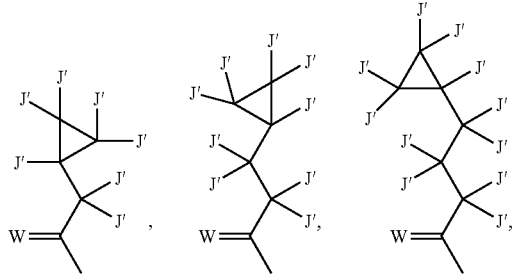

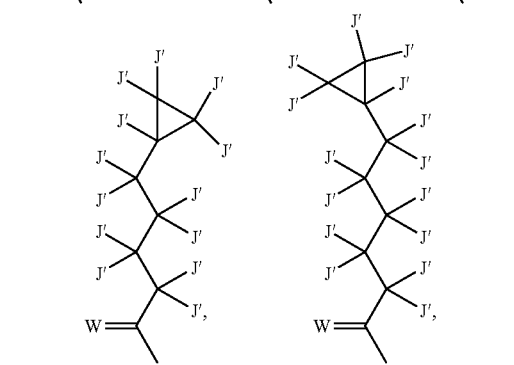

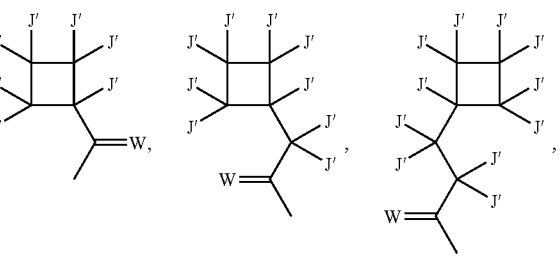

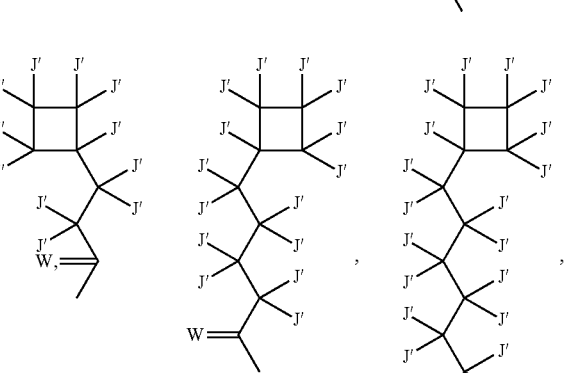

-continued

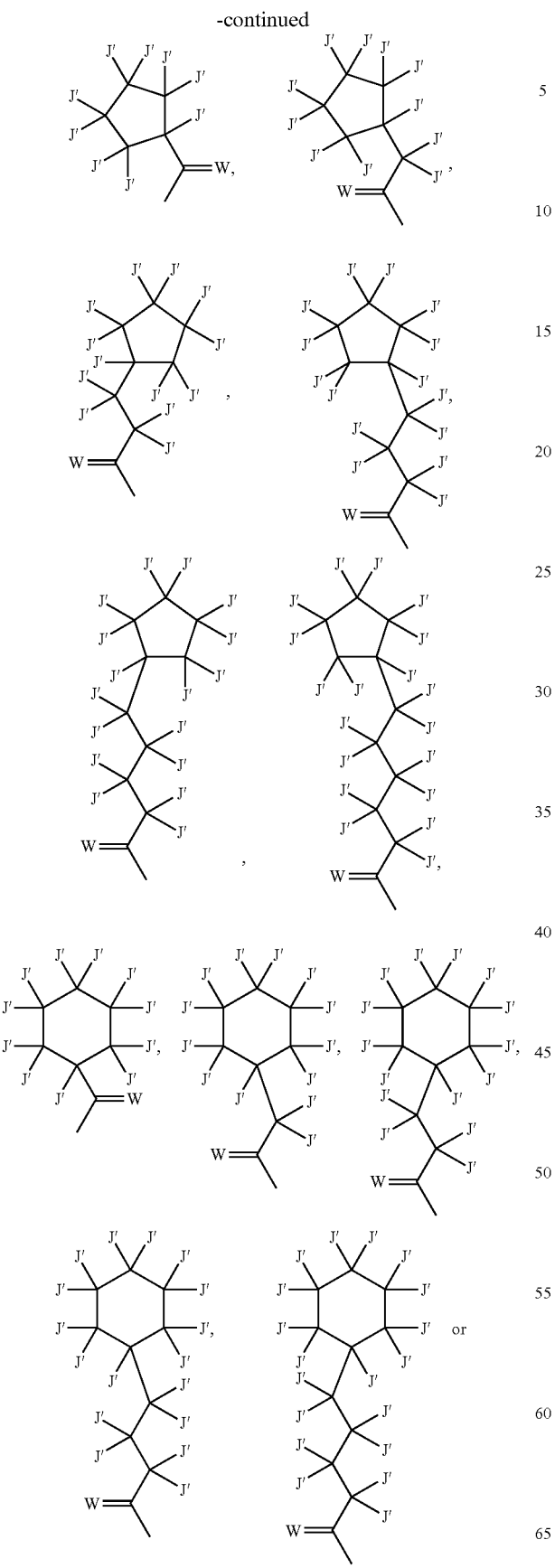

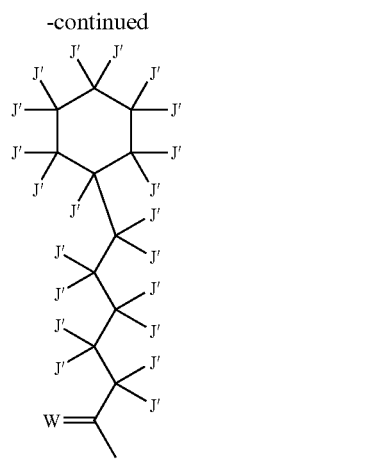

wherein,
each J' is independently H, F, Cl, Br, I, —OH, —SH, —CX₃, —SCX₃ or —OCX₃ wherein each X is independently H, F, Cl, Br or I; and
W is O or S.

15. The method of claim 14, wherein one or more moieties of the formula C(J')₂ in the group is optionally substituted with a moiety of the formula: C=O, C=S, O or S and/or wherein one or more of the moieties of the formula:

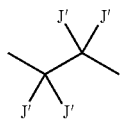

in the group is optionally substituted with a moiety of the formula:

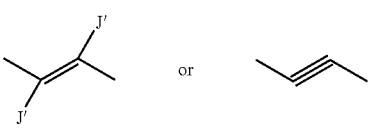

provided that the group is not aromatic when substituted.

16. The method of claim 9, wherein each group independently has the formula:

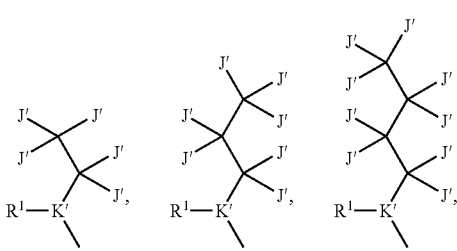

-continued
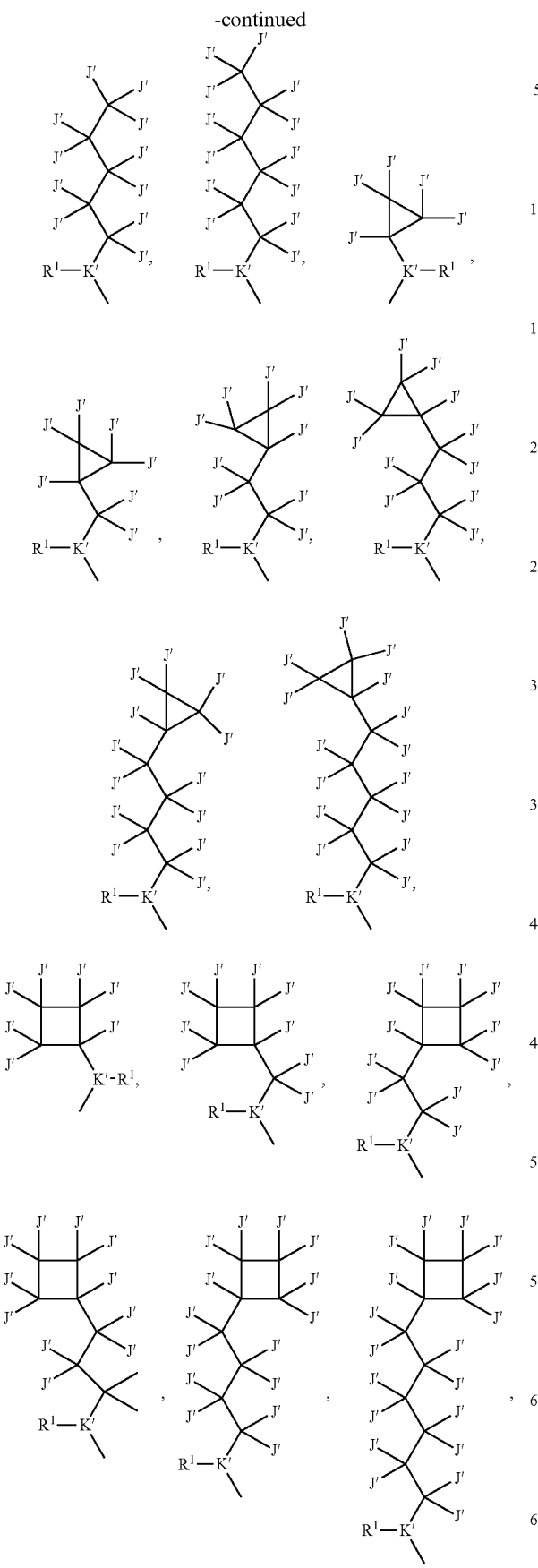
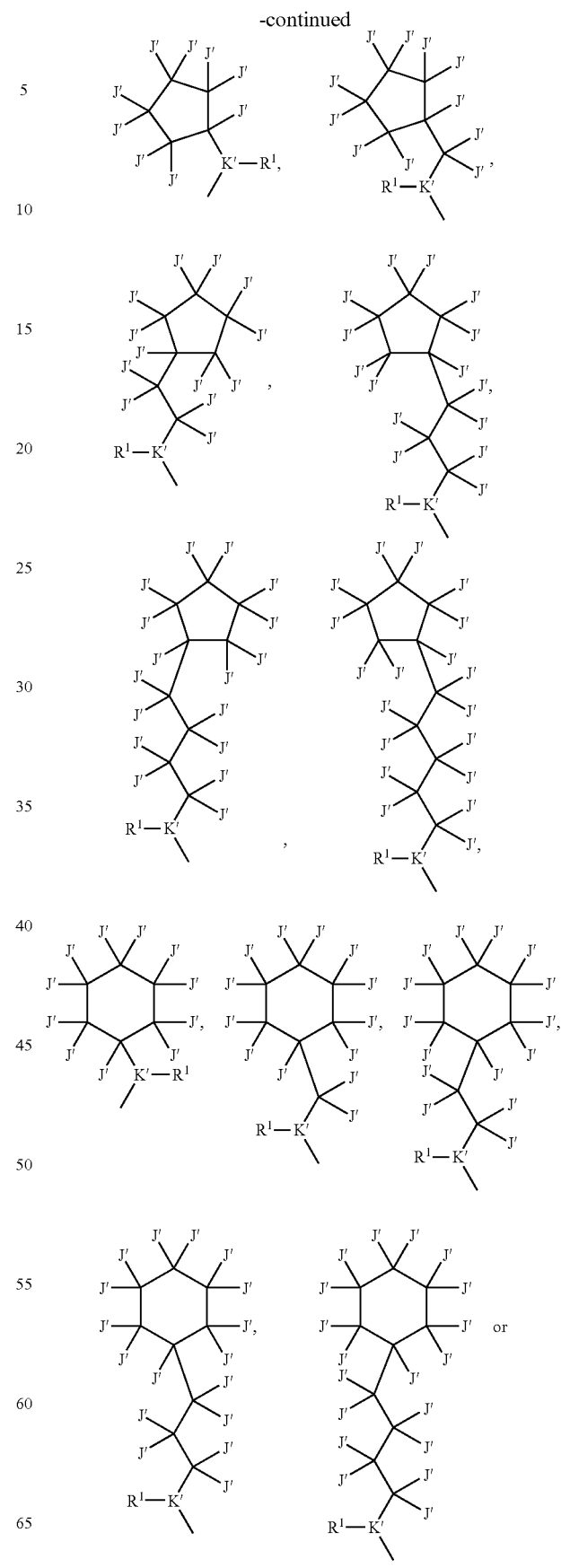

-continued

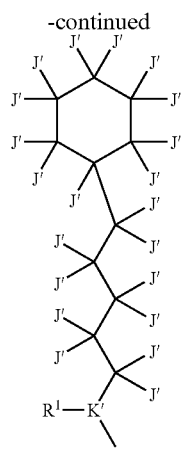

wherein,

K' is N, O or S;

each J' is independently H, F, Cl, Br, I, —OH, —SH, —CX$_3$, —SCX$_3$ or —OCX$_3$ wherein each X is independently H, F, Cl, Br or I; and if K' is O or S, R$^1$ is nothing but if K' is N then R$^1$ is hydrogen or an alkyl group, alkenyl group, alkynyl group, heteroalkyl group, heteroalkenyl group, heteroalkynyl group or heterocyclohydrocarbon group.

17. The method of claim 16, wherein one or more moieties of the formula C(J')$_2$ in the group is optionally substituted with a moiety of the formula: C=O, C=S, O or S and/or wherein one or more of the moieties of the formula:

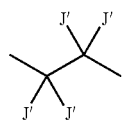

in the group is optionally substituted with a group of the formula:

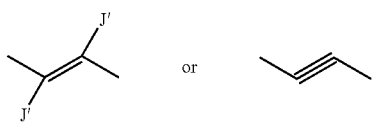

provided that the group is not aromatic when substituted.

18. The method of claim 1, further comprising at least one detectable moiety.

19. The method of claim 1, further comprising at least one amino acid comprising a charged group at physiological pH.

20. The method of claim 1, further comprising at least one universal nucleobase.

21. The method of claim 1, further comprising at least one diaminopurine nucleobase.

22. The method of claim 1, wherein the PNA oligomer further comprises at least one energy donor moiety and at least one energy acceptor moiety.

23. The method of claim 8, wherein the PNA oligomer comprises a C-terminal carboxylic acid group.

24. The method of claim 8, wherein the PNA oligomer is a PNA chimera comprising one or more linked C-terminal nucleosides.

25. The method of claim 1, wherein the PNA oligomer is support bound.

26. The method of claim 1, wherein the PNA oligomer is bound to an array.

27. A method comprising modulating the $T_m$ of a PNA oligomer/NA complex by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, wherein each group comprises a substituted or unsubstituted cyclic hydrocarbon group.

28. The method of claim 27, wherein each cyclic hydrocarbon group is a substituted or unsubstituted cyclopropyl, cyclobutyl, cyclopentyl or cyclohexyl group.

29. A method comprising modulating the $T_m$ of a PNA oligomer/NA complex by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, wherein each group is indirectly linked to the N-terminal amine group and/or to the C-terminal carbonyl carbon.

30. The method of claim 29, wherein each indirectly linked group is the side chain of a non-naturally occurring amino acid.

31. A method comprising modulating the $T_m$ of a PNA oligomer/NA complex by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, wherein the same group is linked to each of the C-terminus and the N-terminus.

32. A method comprising modulating the $T_m$ of a PNA oligomer/NA complex by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, wherein each group is linked directly to the N-terminal amine group, with the further proviso that each group independently has the formula:

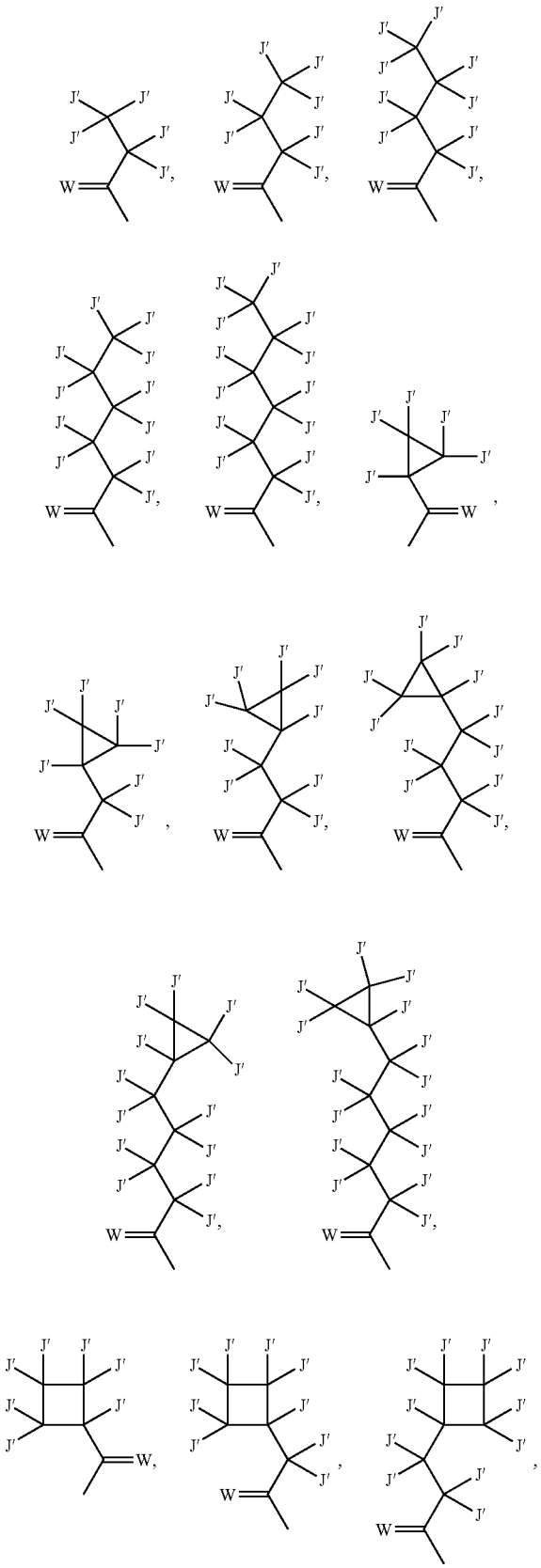
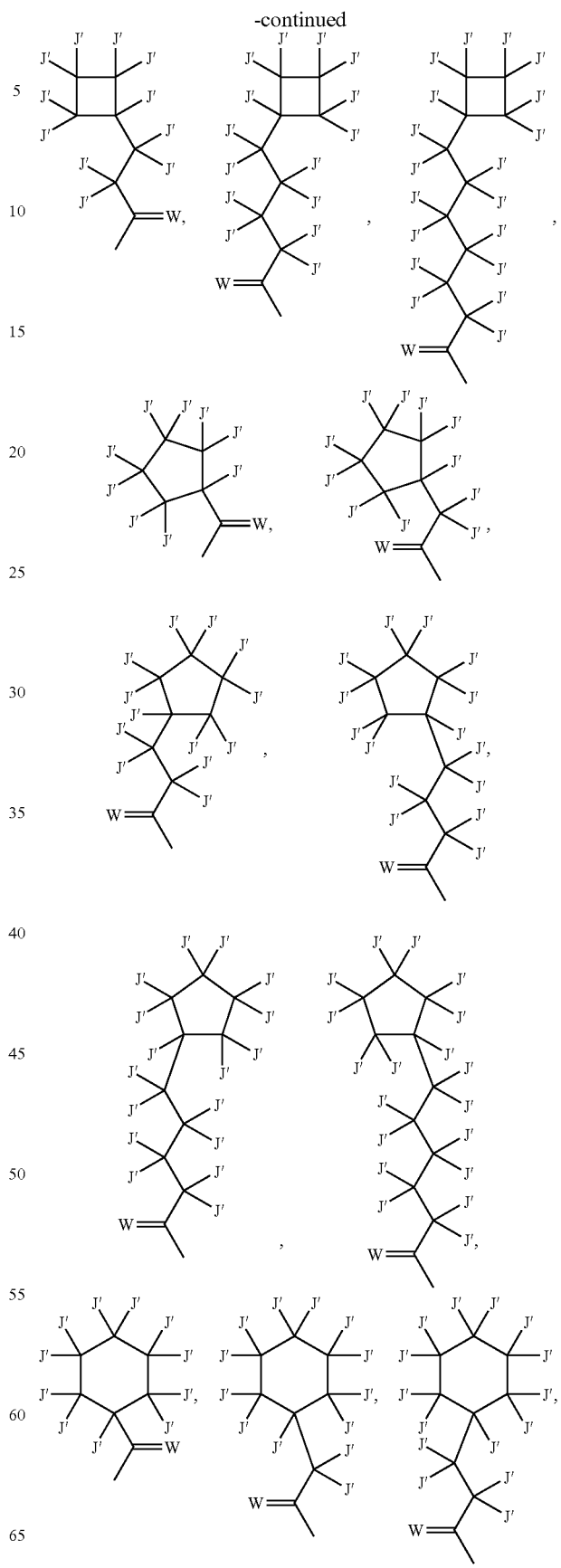

-continued

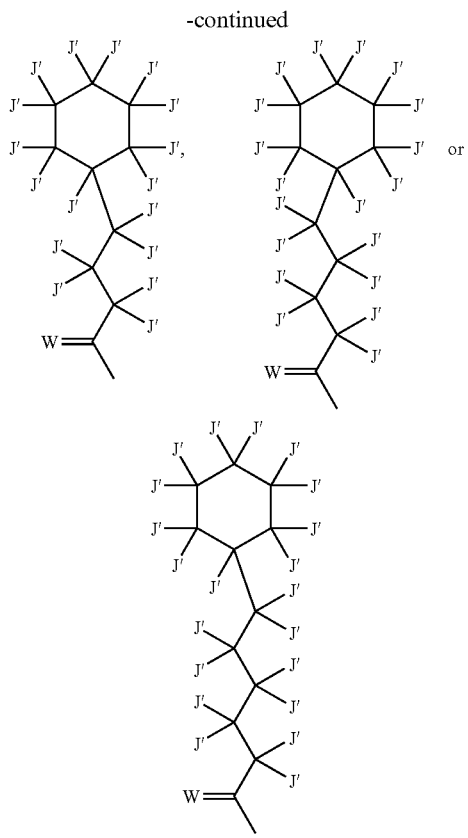

wherein, each J' is independently H, F, Cl, Br, I, —OH, —SH, —CX$_3$, —SCX$_3$ or —OCX$_3$ wherein each X is independently H, F, Cl, Br or I; and W is O or S.

33. The method of claim 32, wherein one or more moieties of the formula C(J')$_2$ in the group is optionally substituted with a moiety of the formula: C=O, C=S, O or S and/or wherein one or more of the moieties of the formula:

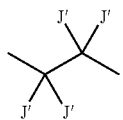

in the group is optionally substituted with a moiety of the formula:

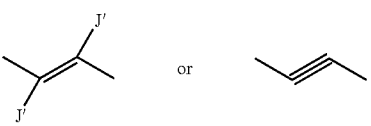

provided that the group is not aromatic when substituted.

34. A method comprising modulating the T$_m$ of a PNA oligomer/NA complex by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, further comprising at least one amino acid comprising a charged group at physiological pH.

35. A method comprising modulating the T$_m$ of a PNA oligomer/NA complex by covalently linking, directly or indirectly, to the PNA oligomer, comprising an N-terminal amine group and a C-terminal carbonyl carbon, at least one alkyl group, alkenyl group, alkynyl group, heteroalkyl group, heteroalkenyl group, heteroalkynyl group or heterocyclohydrocarbon group to the N-terminal amine group and/or to the C-terminal carbonyl carbon of the PNA oligomer used to form the PNA oligomer/NA complex, provided that the group is not an acetyl group or a side chain of a terminally linked natural amino acid, further comprising at least one diaminopurine nucleobase.

* * * * *